US012589071B2

(12) United States Patent
Biffi

(10) Patent No.: US 12,589,071 B2
(45) Date of Patent: Mar. 31, 2026

(54) SUCKABLE AND/OR MELT-IN-MOUTH TABLET BASED ON HYALURONIC ACID AND CHONDROITIN SULPHATE AND SALTS THEREOF

(71) Applicant: SOFAR SWISS SA, Lugano (CH)

(72) Inventor: Andrea Biffi, Bologna (IT)

(73) Assignee: SOFAR SWISS SA, Lugano (CH)

( * ) Notice: Subject to any disclaimer, the term of this patent is extended or adjusted under 35 U.S.C. 154(b) by 0 days.

(21) Appl. No.: 18/586,970

(22) Filed: Feb. 26, 2024

(65) Prior Publication Data

US 2024/0189228 A1 Jun. 13, 2024

Related U.S. Application Data

(63) Continuation of application No. 16/757,999, filed as application No. PCT/IB2018/058552 on Oct. 31, 2018, now abandoned.

(30) Foreign Application Priority Data

Oct. 31, 2017 (IT) ........................ 102017000124424

(51) Int. Cl.
| | |
|---|---|
| *A61K 9/00* | (2006.01) |
| *A61K 9/20* | (2006.01) |
| *A61K 31/728* | (2006.01) |
| *A61K 31/737* | (2006.01) |
| *A61K 33/08* | (2006.01) |
| *A61K 33/10* | (2006.01) |
| *A61K 33/12* | (2006.01) |
| *A61K 47/36* | (2006.01) |
| *A61P 1/04* | (2006.01) |

(52) U.S. Cl.
CPC .......... *A61K 9/0056* (2013.01); *A61K 9/2072* (2013.01); *A61K 9/2095* (2013.01); *A61K 31/728* (2013.01); *A61K 31/737* (2013.01); *A61K 33/08* (2013.01); *A61K 33/10* (2013.01); *A61K 33/12* (2013.01); *A61K 47/36* (2013.01); *A61P 1/04* (2018.01)

(58) Field of Classification Search
None
See application file for complete search history.

(56) References Cited

U.S. PATENT DOCUMENTS

| | | | |
|---|---|---|---|
| 4,163,777 A | 8/1979 | Mitra | |
| 5,178,878 A | 1/1993 | Wehling et al. | |
| 2002/0119104 A1 | 8/2002 | Rosenthal et al. | |
| 2004/0146993 A1 | 7/2004 | Khare et al. | |
| 2006/0147522 A1* | 7/2006 | Olmstead ................. | A61K 9/48 424/464 |
| 2006/0165759 A1 | 7/2006 | Chaudhari et al. | |
| 2009/0208588 A1 | 8/2009 | Brown | |
| 2009/0252709 A1 | 10/2009 | Nose et al. | |
| 2010/0028395 A1 | 2/2010 | Senin et al. | |
| 2010/0105738 A1 | 4/2010 | Mizuno et al. | |
| 2010/0272761 A1 | 10/2010 | Noh et al. | |
| 2011/0038945 A1 | 2/2011 | Gear | |
| 2011/0071106 A1 | 3/2011 | Pizzoni | |
| 2011/0097401 A1 | 4/2011 | Phillips et al. | |
| 2011/0159104 A1 | 6/2011 | Teslenko | |
| 2014/0107064 A1* | 4/2014 | Pizzoni ................ | A61K 31/728 514/54 |
| 2015/0164859 A1 | 6/2015 | Chollet et al. | |
| 2015/0284478 A1 | 10/2015 | Agar et al. | |
| 2019/0125664 A1 | 5/2019 | Biffi | |
| 2019/0125665 A1 | 5/2019 | Biffi | |
| 2019/0262388 A1 | 8/2019 | Biffi et al. | |

FOREIGN PATENT DOCUMENTS

| | | | | |
|---|---|---|---|---|
| CN | 104707127 A | * | 6/2015 | |
| EP | 2581090 A1 | | 4/2013 | |
| JP | S6147418 A | | 3/1986 | |
| WO | 2005032554 A1 | | 4/2005 | |
| WO | 2010136872 A2 | | 12/2010 | |
| WO | WO 2010136872 | * | 12/2010 | |
| WO | 2017055909 A1 | | 4/2017 | |
| WO | WO 2017/055909 | * | 4/2017 | |

OTHER PUBLICATIONS

Lewis et al. "Toxicological assessment of chondroitin sulfate oligosaccharide" 2023.*
Chemical Book Hyaluronic acid.*
Chemical Book Sodium hyaluronate.*
Palmeri "Fixed combination of hyaluronic acid and chondroitin sulphate oral formulation in a randomized double blind, placebo controlled study for the treatment of symptoms in patients with non-erosive gastroesophageal reflux" 2013.*
ChemIDplus. Feb. 12, 2022.
Abstract of WO2017/055909 from CAPLUS (Year: 2017).
Boarino et al. (2020) "Symptomatic response to GERDOFF® in patients with gastro-esophageal reflux isease and poor response to alginates: an exploratory, post-market, open-label study" Turkish Journal Df Gastroenterology 31:6466-73.
Chemical Abstracts Registry No. 9004-61-9, from STN (Year: 2023).
Fagron Safety Data Sheet, Oct. 26, 2014.
Horn et al., "Similarities and differences among delayed-release proton-pump inhibitor formulations", Alimentary pharmacology & therapeutics, (2005), 22 (Suppl. 3): 20-24.
Irirpude et al., "Rabeprazole sodium delayed-release multiparticulates: Effect of enteric coating layers on product t>erformance", J Adv Pharm Technol Res, 2011, 2(3): 184-191.

(Continued)

*Primary Examiner* — Danah Al-Awadi

(74) *Attorney, Agent, or Firm* — Silvia Salvadori, P.C.; Silvia Salvadori

(57) ABSTRACT

The present invention relates to a suckable and/or melt-in-mouth tablet based on hyaluronic acid and chondroitin sulphate and/or salts thereof.

4 Claims, 6 Drawing Sheets

(56) References Cited

OTHER PUBLICATIONS

Figure 1:
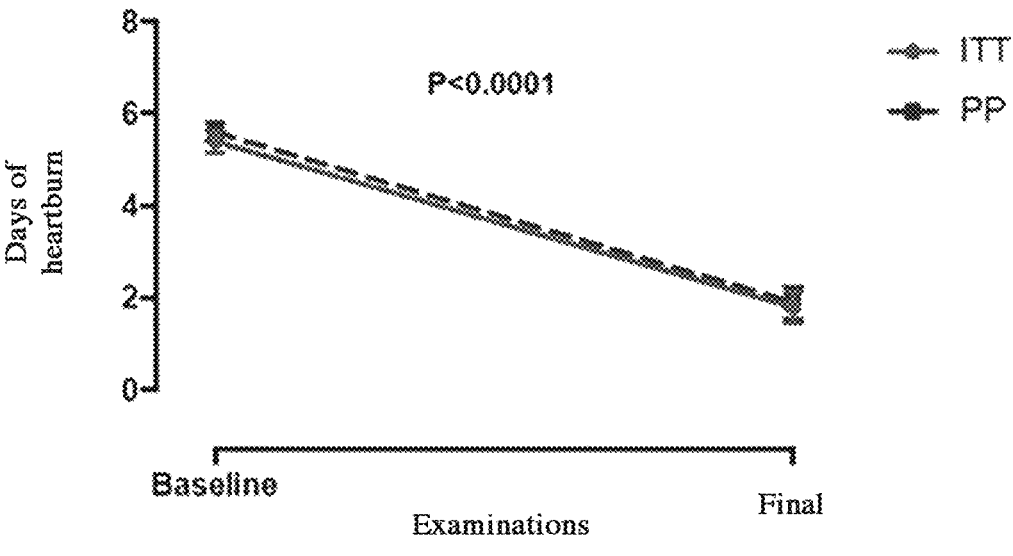

Morelli, et al., "An open-label, parallel, multiple-dose study comparing the pharmacokinetics and gastric acid uppression of rabeprazole extended-release with esomeprazole 40 mg and rabeprazole delayed-release 20 mg in healthy volunteers", Alimentary pharmacology & therapeutics, (2011), 33: 845-854.

Norman et al., "What you need to know when you prescribe a proton pump inhibitor", Frontline Gastroenterology, 011, 2: 199-205.

Palmieri et al., "Fixed combination of hyaluronic acid and chondroitin-sulphate oral formulation in a randomized double blind, placebo controlled study for the treatment of symptoms in patients with non-erosive gastroesophageal reflux" 2013.

Palmieri, "Preliminary clinical experience with a new natural compound in the treatment of oesophagitis and gastritis: symptomatic effect", Trends Med, 2009, 9(4): 219-225.

Plbe et al., "A proton-pump inhibitor expedition: the case histories of omeprazole and esomeprazole", Nature reviews rug discovery, (2003), 2: 132-139.

Popescu C. Why Oral Disintegrating Tablets? Drug Delivery Magazine, issue 69 Ouly 2016).

Ptake et al., "Characteristics of the Novel Potassium-Competitive Acid BlockerVonoprazan Fumarate (TAK-438)", Mv Ther., 2016, 33(7): 1140-1157.

Pumortier et al., "A Review of Poloxamer 407 Pharmaceutical and Pharmacological Characteristics", Pharmaceutical Research, 2006, 23(12): 2709-2728.

Savarino et al. "Drugs for improving esophageal mucosa defense: where are we and where are we going?". Aug. 2017.

Sigma-Aldrich Poloxamer 407.

Smart et al., "Comparison of a dimethicone/antacid (Asilone gel) with an alginate/antacid (Gaviscon liquid) in the management of reflux oesophagitis", Journal of the Royal Society of Medicine, 1990, 83: 554-556.

WHO monographs on selected medicinal plants: Aloe Vera Gel, World Health Organization, 1999, 1:43-49.

Olbe et al., "A proton-pump inhibitor expedition: the case histories of omeprazole and esomeprazole", Nature review drug discovery, (2003), 2:132-139.

Otake et al., "Characteristics of the novel potassium-competitive acid blocker vonoprazan fumarate (TAK-438)", Adv Ther. 2016, 33(7): 1140-1157.

Tirpude et al., "Rabeprazole sodium delayed-release multiparticulates: effect of enteric coating layers on product performance", J Adv Technol Res 2011 2(3): 184-191.

Durmortier et al., "A review of poloxamer 407 pharmaceutical and pharmacological characteristics", Pharmaceutical Research, 2006, 23(12): 2709-2728.

Chemical Abstract Registry No. 9004-61-9, from STN (Year: 2023).

* cited by examiner

SUCKABLE AND/OR MELT-IN-MOUTH TABLET BASED ON HYALURONIC ACID AND CHONDROITIN SULPHATE AND SALTS THEREOF

This U.S. Application is a continuation of U.S. Ser. No. 16/757,999 filed Apr. 21, 2020, which is a National Stage Application of PCT/IB2018/058552, filed on Oct. 31, 20218, which claims priority from and the benefit of Italian Application no. 1020170000124424, filed Oct. 31, 2017, the contents of which are all incorporated herein by reference in their entireities.

The present invention relates to a chewable and/or suckable and/or melt-in-mouth and/or orally dissolving tablet based on hyaluronic acid and chondroitin sulphate and/or salts thereof.

It is well known that a considerable part of the western population, estimated to range from about 10% to about 30%, suffers from discomforts or disorders linked to gastroesophageal reflux disease (GERD). The most common disorders and discomforts are heartburn, acidity and regurgitation.

Gastroesophageal reflux is the involuntary and unconscious passage of a part of gastric contents into the esophagus, without the joint participation of gastric and abdominal muscles. Gastroesophageal reflux is substantially the upflow of acidic contents into the esophagus, the 25-30 cm long canal that connects the mouth with the stomach. When someone eats, the esophagus, aided by the force of gravity and a series of rhythmic movements, is able to make swallowed food progress downward. The passage of the alimentary bolus into the stomach is regulated by the lower esophageal sphincter, a special muscular valve that opens to allow the transit of food, belching and vomiting. Precisely this sphincter, by closing, prevents the upflow, for example, of the acidic juices present in the stomach. Gastroesophageal reflux occurs when the esophageal sphincter is released at an inappropriate time, thus allowing the upward passage of gastric contents. Due to its acidity, this material irritates the esophageal mucosa, triggering the symptoms typical of the disorder. The condition becomes pathological when the reflux occurs too often or when the gastric contents are excessively acidic.

The typical symptoms of gastroesophageal reflux disease are represented by: retrosternal burning (pyrosis), regurgitation and the perception of the upflow of acidic material along the esophagus. Considering these two symptoms (burning and regurgitation), the reflux pathology appears to affect about 30% of Italians. In some patients, reflux disease is associated, in the acute phase, with an esophageal spasm. This involuntary contraction can cause a retrosternal pain similar to that of angina pectoris. Chest pain due to gastroesophageal reflux is very often associated with heavy meals and gets worse with exertion and in a lying position.

Dysphagia (difficulty in the progression of food along the esophagus) is another typical symptom of reflux disease.

There also exists a particular set of symptoms which, despite being linked to reflux disease, are atypical. These are the so-called symptoms with an extraesophageal location, which can affect the throat and respiratory tract (extraesophageal reflux or laryngopharyngeal reflux (LPR). In fact, often patients with typical symptoms of gastroesophageal reflux also suffer from other disorders such as hoarseness, dysphonia, asthma, chronic coughing, laryngitis or pharyngitis. In these cases, the acid refluxate manages to flow upward until reaching the throat, where it is nebulised by the air breathed in. During inspiration, these droplets can reach the lungs, where they provoke specific problems such as coughing and asthma. All of these atypical disorders can be present also in the absence of the classic symptoms of gastroesophageal reflux disease.

Gastroesophageal reflux disease is a nosological entity that includes a spectrum of manifestations that include GERD (Gastroesophageal Reflux Disease) and is in turn divided into ERD (Erosive Reflux Disease), NERD (Non-Erosive Reflux Disease), complicated GERD, manifestations due to weakly acid reflux, biliary reflux, extraesophageal manifestations, and others.

As mentioned, gastroesophageal reflux disease includes a non-erosive reflux or non-erosive reflux disease (acronym NERD) characterised by the presence of gastroesophageal reflux and/or extraesophageal reflux (or laryngopharyngeal reflux) in the absence of endoscopic damage visible under gastroscopy, since the refluxate containing stomach acid does not cause esophagitis.

Therefore, in the light of the foregoing, even a partial reflux of gastric contents from the stomach to the esophagus leads to bothersome symptoms, with or without involvement of the mucosa.

Numerous experimental data drawn from randomised studies have shown that benefits can be obtained as a result of the inhibition of gastric acid secretion: reducing the acidity of gastric juices improves the symptoms due to reflux and enables esophagitis to be improved and in some cases cured.

A standard dose of proton pump inhibitors (PPIs) can lead to the cure of reflux esophagitis in over 80% of patients.

However, their effectiveness in giving relief following a regurgitation is very modest, and considerably greater than the relief reached in the case of the heartburn. Furthermore, about 20% of patients correctly diagnosed with GERD and properly treated do not respond to PPI-based therapy at the standard dose.

Among medications for the treatment of the gastroesophageal reflux, alginate-based formulations capable of forming a so-called floating "raft" inside the stomach are used to treat heartburn and reflux esophagitis. In the presence of gastric acidity, alginates precipitate and form a gel. The bicarbonate, usually present in these formulations as calcium or potassium bicarbonate, is converted into carbon dioxide, which is trapped inside the precipitated gel. The gel is then converted into a foam that floats on the surface of the gastric contents, like a "raft" on water.

Alginate-based therapies increase the probability of resolution of GERD symptoms when compared with a placebo or antacids but to date, unfortunately, the experimental data regarding their effectiveness compared to treatments with common PPIs and with histamine H2 receptor antagonists (or H2 blockers) have not been conclusive or satisfactory.

Furthermore, in clinical practice it often occurs that a fairly high portion of treated patients must be treated again, since their symptoms have not improved despite their undergoing a treatment with alginates alone or a treatment in which alginates have been administered in addition to a therapy with PPIs. Or else it may occur that a significant percentage of patients need to continue taking drugs even 3-4 years after the diagnosis; this percentage can reach as high as 70% of the total patients who go to gastroenterological centres.

In view of the foregoing, given the high frequency of GERD symptoms in the western population and the growing prevalence of patients who do not respond to a therapy with alginates, standard PPIs or alginates in association with standard PPIs, there is an urgent clinical need to develop new therapeutic strategies.

There thus remains a need to be able to have new formulations capable of treating patients who are non-responsive or poorly responsive to the known alginate-based or PPI-based, or alginate- and PPI-based treatments so that said formulations may represent a new improved therapy that is well tolerated and has no (or few and/or modest) side effects, for the treatment of patients affected by GERD and/or extraesophageal symptoms and disorders.

The Applicant has realised that a mechanical protection is useful for preventing possible damage to the esophageal mucosa caused by gastric reflux.

After a long, intense research and development activity, the Applicant has developed a novel composition (or formulation) in solid form able to provide an adequate response to the above-mentioned needs.

FIGURES

FIG. 1: number of days of heartburn per week from examination V0 to examination V1 as recorded in the clinical study of Experimental Part (I).

Figure 2:
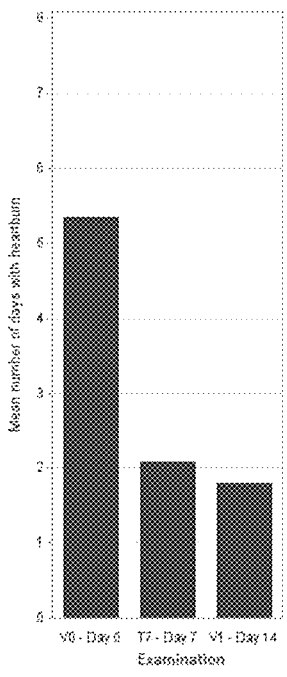

FIG. 2: number of days of heartburn per week from examination V0, to examination T7 and examination V1 as recorded in the clinical study of Experimental Part (I).

Figure 3:
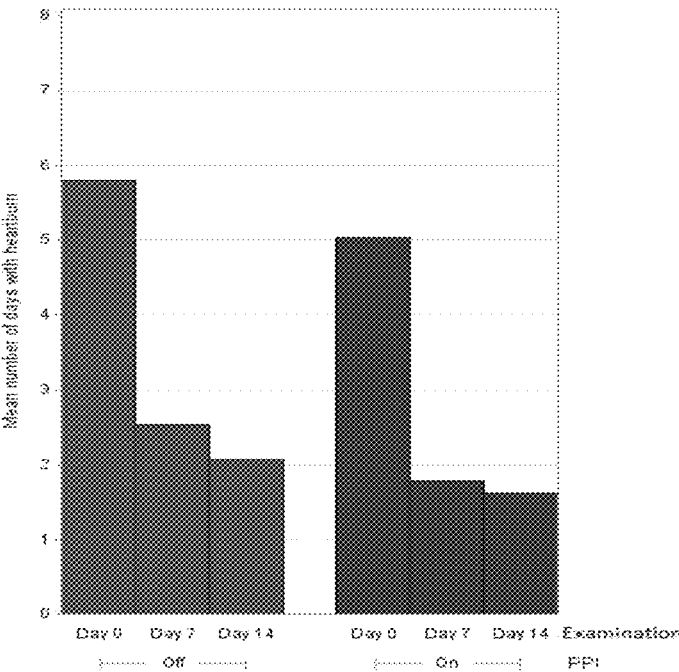

FIG. 3: number of days of heartburn per week from examination V0, to examination T7 and examination V1 as recorded in the clinical study of Experimental Part (I) for subjects with or without a concomitant treatment with PPIs.

Figure 4:
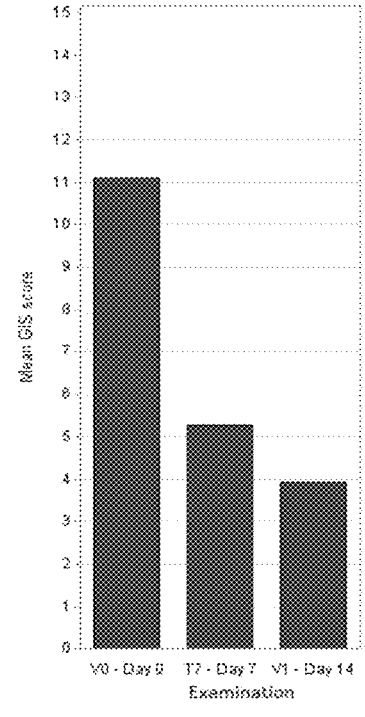

FIG. 4: average score on the GIS questionnaire from examination V0, to examination T7 and to examination V1 as recorded in the clinical study of Experimental Part (I).

Figure 5:
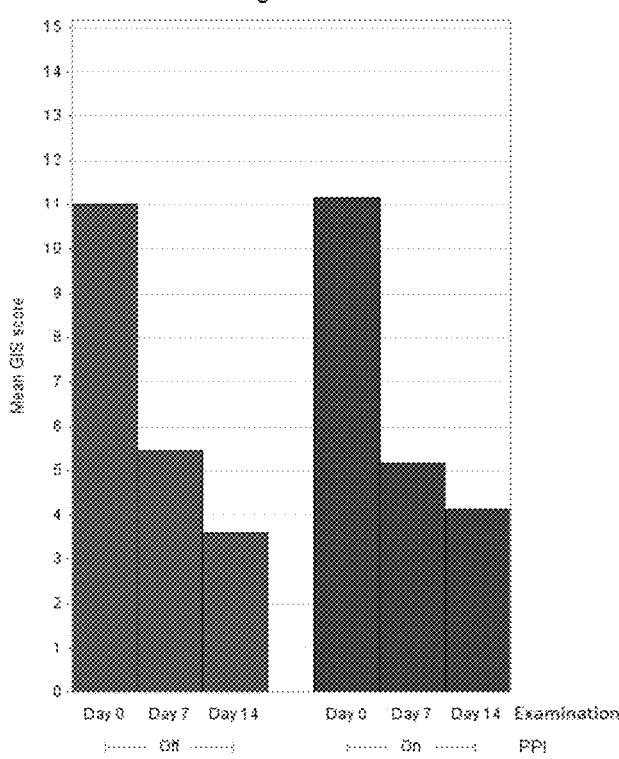

FIG. 5: average score on the GIS questionnaire from examination V0, to examination T7 and to examination V1 as recorded in the clinical study of Experimental Part (I) for subjects with or without a concomitant treatment with PPIs.

Figure 6:
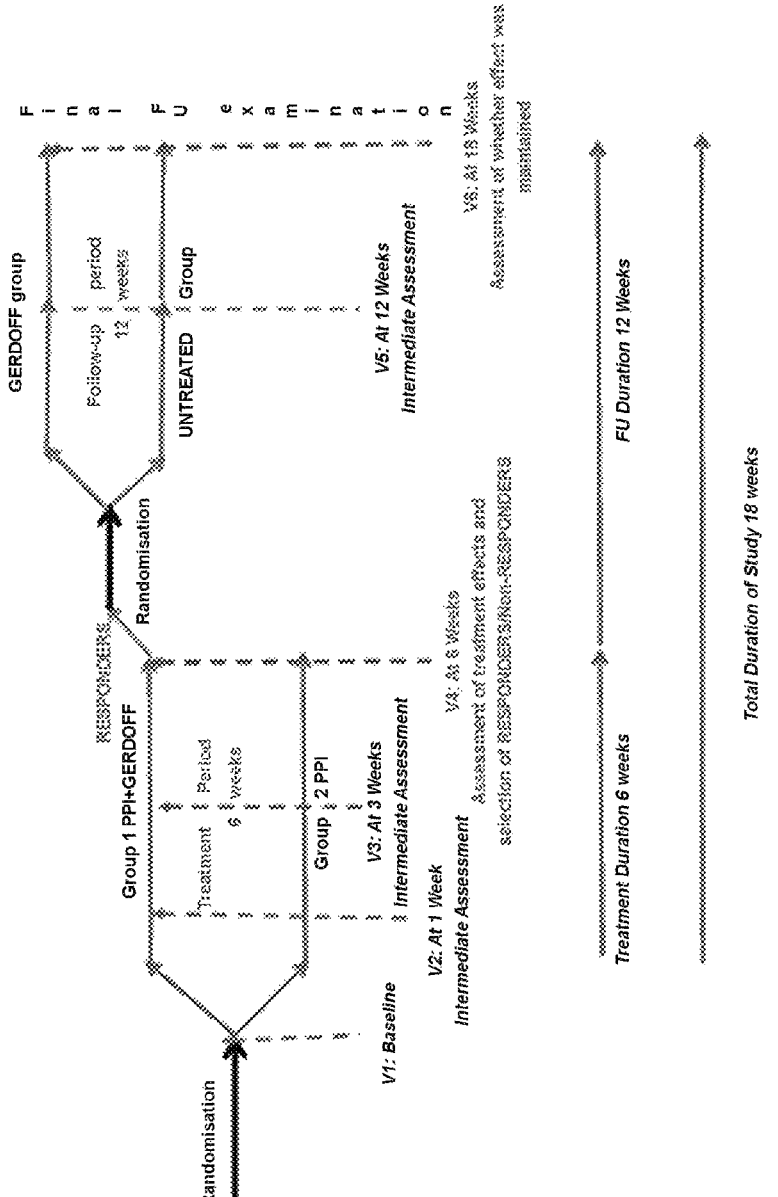

FIG. 6: clinical study design of Experimental Part (II).

Figure 7:
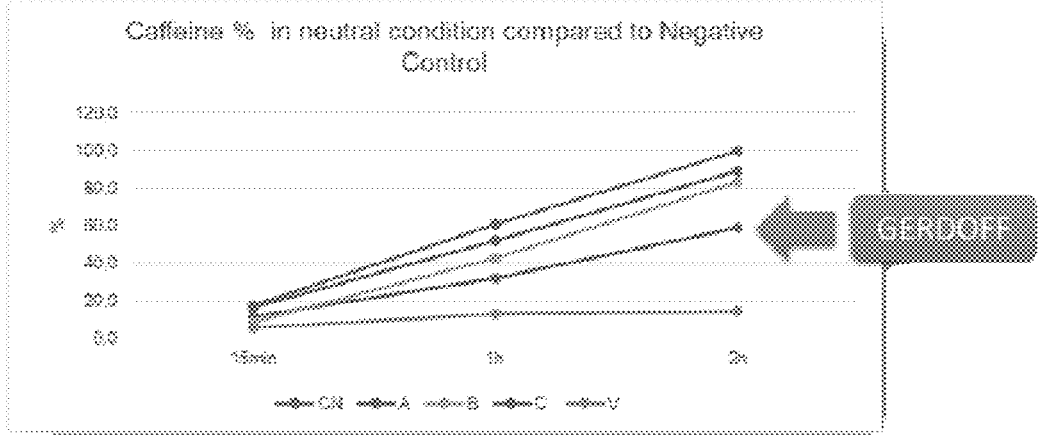

FIG. 7: in vitro model of esophageal epithelium, % caffeine penetration after 2 hours versus the negative control of 100% under neutral pH conditions; reference to Table 7.

Figure 8:
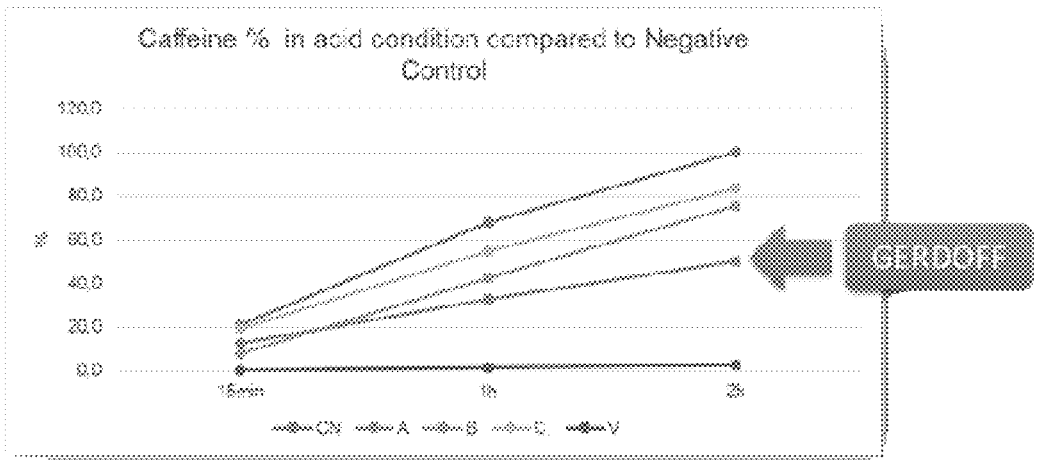

FIG. 8: in vitro model of esophageal epithelium, % caffeine penetration after 2 hours versus the negative control of 100% under acidic pH conditions; reference a Table 8.

Figure 9:
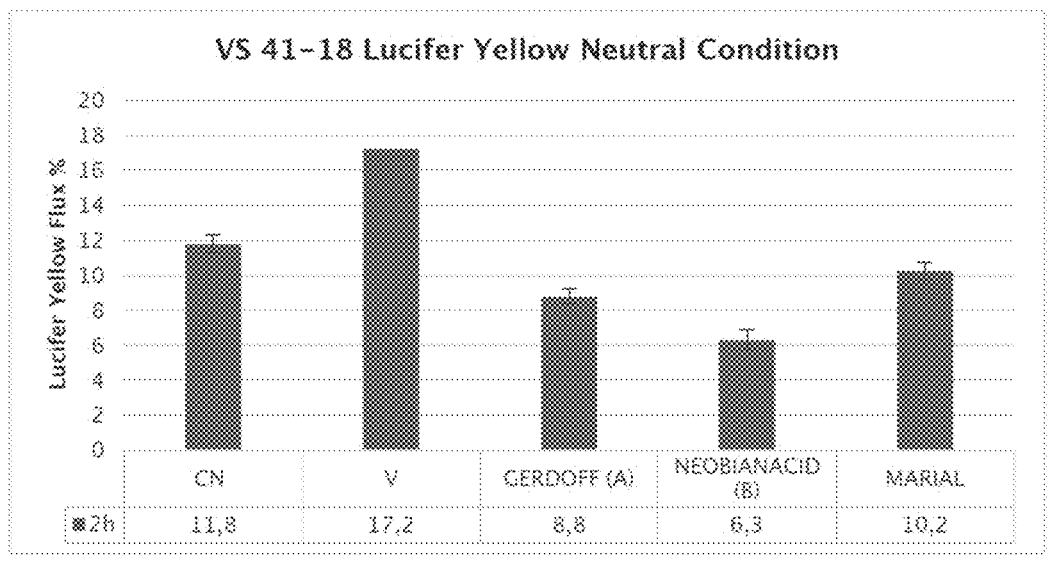

FIG. 9: in vitro model of esophageal epithelium, % Lucifer Yellow flow at 2 hours versus time 0 under neutral pH conditions.

DESCRIPTION OF THE INVENTION

The subject matter of the present invention relates to a composition for oral use in the solid form of a chewable and/or suckable and/or melt-in-mouth and/or orally dissolving tablet containing (i) a hyaluronic acid, or a salt thereof, and (ii) a chondroitin, or a salt thereof, having the technical features as defined in the accompanying independent claim.

The subject matter of the present invention further relates to a composition for oral use in the solid form of a chewable and/or suckable and/or melt-in-mouth and/or orally dissolving tablet which, in addition to containing (i) a hyaluronic acid, or a salt thereof, and (ii) a chondroitin, or a salt thereof, further contains (iii) a (basic) substance with antacid properties selected from the group comprising or, alternatively, consisting of a salt in the form of an oxide, a hydroxide, a carbonate, a bicarbonate, a silicate, a sulphate or a citrate of an alkali metal or alkaline earth metal or of a metal (III) or other substances with an antacid/buffer effect, having the technical features as defined in the accompanying independent claim.

The subject matter of the present invention further relates to a composition for oral use in the solid form of a chewable and/or suckable and/or melt-in-mouth and/or orally dissolving tablet which, in addition to containing (i) a hyaluronic acid, or a salt thereof, and (ii) a chondroitin, or a salt thereof, and (iii) a (basic) substance with antacid properties, also further comprises an additional (iv) proton pump inhibitor (PPI) compound having the technical features as defined in the accompanying independent claim.

The subject matter of the present invention further relates to a composition for oral use in the solid form of a chewable and/or suckable and/or melt-in-mouth and/or orally dissolving tablet which comprises (i) and (ii); or (i), (ii) and (iii); or (i), (ii) and (iv); or (i), (ii), (iii) and (iv), as defined above; said composition being for use in a method for the treatment of patients affected by GERD and/or extraesophageal symptoms or disorders caused by the upflow of gastric contents from the stomach to the oral cavity and/or ulcers or lacerations in the mucosa, having the technical features as defined in the accompanying independent claim.

By virtue of said chewing and/or sucking and/or melting in the mouth, components (i) and (ii); or (i), (ii) and (iii) or (i), (ii) and (iv); or (i), (ii), (iii) and (iv) comprised in the composition in the solid form of a chewable and/or suckable and/or melt-in-mouth and/or orally dissolving tablet for use in the aforesaid treatment methods form, together with the saliva of the subject to whom they are administered, a viscous gel that adheres to the mucosa of the various anatomical parts from the oral cavity to the stomach by swallowing.

Said composition comprising (i) and (ii); or (i), (ii) and (iii); or (i), (ii) and (iv); or (i), (ii), (iii) and (iv), as defined above for use in a method for the treatment of patients affected by GERD does not comprise bioadhesive carriers, such as, for example, polymeric bioadhesive carriers of a synthetic nature, e.g. poloxamers (Lutrol®).

The subject matter of the present invention further relates to a composition for oral use in the solid form of a chewable and/or suckable and/or melt-in-mouth and/or orally dissolving tablet which comprises (i) and (ii); or (i), (ii) and (iii); or (i), (ii) and (iv); or (i), (ii), (iii) and (iv), as defined above; said composition being for use in a method for the treatment of patients affected by GERD and/or extraesophageal symptoms or disorders caused by the upflow of gastric contents from the stomach to the oral cavity and/or ulcers or lacerations in the mucosa, wherein the subjects treated with the composition of the invention also undergo a concomitant treatment with PPIs having the technical features as defined in the accompanying independent claim.

The subject matter of the present invention further relates to a composition for oral use in the solid form of a chewable and/or suckable and/or melt-in-mouth tablet which comprises (i) and (ii); or (i), (ii) and (iii); or (i), (ii) and (iv); or (i), (ii), (iii) and (iv); said composition being for use in a method for the treatment of a subpopulation of GERD patients represented by patients who have been diagnosed with gastroesophageal reflux but have demonstrated to be non-responsive or poorly responsive to treatments with alginates. Said GERD subpopulation treated with the composition of the invention may, or alternatively, may not undergo a concomitant treatment with PPIs.

In the context of the present invention, the expression "patients diagnosed with gastroesophageal reflux who are non-responsive or poorly responsive to treatments with alginates" should be understood as illustrated below in Table 1; more briefly, it may be said that the patients considered poorly responsive or non-responsive to alginates in this context are patients who report at least 1 episode of heartburn per day for at least 4 days, also not consecutive, during the course of a treatment of at least two weeks with alginates taken 4 times a day.

The subject matter of the present invention further relates to a method for the treatment of subjects affected by GERD and/or extraesophageal symptoms or disorders or symptoms caused by the upflow of gastric contents from the stomach to the oral cavity and/or ulcers or lacerations in the mucosa, wherein said treatment method comprises administering to said subjects a composition for oral use in the solid form of a chewable and/or suckable and/or melt-in-mouth and/or orally dissolving tablet which comprises (i) and (ii); or (i), (ii) and (iii); or (i), (ii) and (iv); or (i), (ii), (iii) and (iv), as defined above. Said subjects may, or alternatively, may not undergo a concomitant treatment with PPIs.

In an embodiment, said treatment method is recommended for a subpopulation of GERD patients represented by patients who have been diagnosed with gastroesophageal reflux but have demonstrated to be non-responsive or poorly responsive to treatments with alginates; said subpopulation administered with the composition of the invention can undergo, or alternatively, not undergo a concomitant treatment with PPIs.

Preferred embodiments of the present invention will be set forth in the detailed description that follows, without any intention of limiting the scope of the present invention.

As noted, it is important, among other things, to create a barrier protection of a mechanical type in order to prevent the damage caused to the gastroesophageal mucosa by gastric (gastroesophageal) reflux or extraesophageal reflux.

The Applicant has found that, in order to maximise the effect of the hyaluronic acid, or salts thereof, chondroitin (for example in the form of chondroitin sulphate), or salts thereof (for example in the form of chondroitin sulphate sodium, preferably chicken derived), in the treatment of disorders and symptoms caused or provoked by gastroesophageal reflux, or in the treatment of extraesophageal disorders and symptoms caused by the upflow of so-called refluxate, or in the treatment of ulcers or lacerations provoked in the mucosa or in the tissues lining the various anatomical regions present, from the stomach along the entire esophagus and the oral cavity (including the larynx, pharynx and upper respiratory tract), it is important that the above-mentioned compounds, orally administered, be present in a composition/formulation in a monolithic solid form, for example in the form of a chewable and/or suckable and/or melt-in-mouth and/or orally dissolving tablet or lozenge or pill.

The reason for having a composition or formulation in a chewable and/or suckable and/or melt-in-mouth monolithic solid form, without swallowing it, is given by the fact that saliva starts dissolving the hyaluronic acid, or a salt thereof, and the chondroitin (for example in the form of chondroitin sulphate), or a salt thereof (for example in the form of chondroitin sulphate sodium, preferably chicken derived), and optionally a basic substance present therein, while also incorporating a part of the same within it and thus forming a gelatinous substance with a certain viscous and adhesive property. Furthermore, the dissolution of the composition in solid form triggers the production of other saliva, since there is a stimulation of the salivary glands. It is important that the hyaluronic acid, or a salt thereof, and chondroitin, or a salt thereof, have the necessary time to come into contact with saliva so as to stimulate the further secretion of saliva by the salivary glands, and give rise to a gelatinous substance with a certain viscous and adhesive property.

Saliva contains, among other substances, electrolytes such as, for example, sodium ions, potassium ions and bicarbonate ions, mucus composed of glycosaminoglycan and glycoproteins, and enzymes. It is important that the hyaluronic acid and chondroitin present in the composition of the present invention, for example in the form of a tablet, can both dissolve slowly with saliva when the composition of the present invention, in the form, for example, of a tablet, is in the mouth and remains there until it is completely gone. The tablet of the present invention must be chewed or sucked or dissolved in the mouth. In this manner, a substance with a gelatinous consistency (a sort of viscous gel) and a certain viscous and adhesive property will form which, once swallowed, will be capable of progressively and evenly and continuously lining the oral cavity, laryngopharynx and esophagus until gradually reaching the stomach. For this reason, it is preferable that the composition of the present invention, for example in the form of a tablet or lozenge, is not swallowed as such, or broken up into smaller pieces or swallowed in pieces. For example, it is preferable that the composition of the present invention in the form of a tablet or lozenge remains in the mouth so as to be slowly dissolved in a time comprised from 1 minute to 60 minutes, preferably from 3 minutes to 40 minutes, more preferably from 5 minutes to 20 minutes.

By progressively incorporating a part of the hyaluronic acid, or a salt thereof, and chondroitin, or a salt thereof, and optionally a part of a basic substance, the saliva forms a substance with a gelatinous consistency and a certain viscous and adhesive property that performs a first coating action with a natural buffer effect against the acidity present on the mucosa, thanks to the presence also, but not only, of the carbonate ions present in the saliva itself.

Furthermore, the hyaluronic acid and chondroitin (for example chondroitin sulphate), which begin to dissolve slowly from the composition in a solid monolithic form, while it is gradually dissolved in the mouth, gradually descend from the oral cavity into the esophagus until reaching the stomach, providing an additional action, which in this case will be of both protection and repair of the mucosa and any damaged tissues present in the various anatomical regions.

In the context of the present description, the composition or formulation in a chewable monolithic solid form is not a chewable gum or deformable tablet.

In the context of the present description, the composition or formulation in a chewable solid form is not a solid form, for example a tablet, to be broken into pieces and/or swallowed whole or in pieces with saliva rapidly without leaving time for the saliva to dissolve components (i), (ii) and, optionally, (iii) as defined above and comprised therein, and without leaving time for the saliva to incorporate said components (i), (ii) and, optionally, (iii) within it so as to form a gelatinous substance with a certain viscous and adhesive property.

Preferred embodiments (RPn) of the present invention are set forth below.

RP1. A composition for oral use in the solid form of a chewable and/or suckable and/or melt-in-mouth and/or orally dissolving tablet, preferably a suckable and/or melt-in-mouth and/or orally dissolving tablet, comprising a mixture which comprises or, alternatively, consists of a hyaluronic acid, or a salt thereof, and a chondroitin, or a salt thereof and, optionally, at least one food or pharmaceutical grade excipient or additive; said composition being for use:

i) in the treatment of subjects with disorders or symptoms caused or provoked by gastroesophageal reflux (GERD), or preferably erosive GERD, or ii) in the treatment of subjects with extraesophageal disorders or symptoms caused by the upflow of gastric contents and/or gastric vapours from the stomach along the oral cavity (also known as refluxate, which comprises pepsin, acid and/or mildly acidic or non-acidic but irritating contents), or iii) in the treatment of subjects with ulcers or lacerations provoked in the gastric mucosa (stomach lining), in the esophageal and laryngopharyngeal mucosa or the tissues lining the oral cavity, so as to protect the mucosa and the tissues of the various anatomical regions from the damage provoked thereto.

RP1b. A composition for use according to RP1, wherein said solid form of a chewable and/or suckable and/or melt-in-mouth and/or orally dissolving tablet, or the like, has the function of causing the dissolution of at least said hyaluronic acid, or a salt thereof, and said chondroitin, or a salt thereof and in the saliva of the subject to whom said composition is administered so as to form a viscous gel that adheres to the mucosa of the various anatomical parts from the oral cavity to the stomach by swallowing of said gel.

RP2. A composition for use according to RP1 or RP1b, wherein said hyaluronic acid, or a salt thereof, and said chondroitin, or a salt thereof, preferably both have an average molecular weight comprised from greater than about 1 KDa to less than about 1,000 KDa.

RP3. The composition for use according to RP1, RP1b or RP2, wherein said hyaluronic acid is preferably a linear, branched, cross-linked or substituted hyaluronic acid having an average molecular weight comprised from about 200 KDa to about 800 KDa; more preferably, said linear, branched, cross-linked or substituted hyaluronic acid has an average molecular weight comprised from about 400 KDa to about 600 KDa.

RP4. The composition for use according to any one of the preceding RP1-RP3, wherein said hyaluronic acid is preferably the hyaluronic acid CAS no. 9004-61-9.

RP5. The composition for use according to any one of the preceding RP1-RP4, wherein said hyaluronic acid is preferably in the form of a salt, such as a hyaluronate of an alkali metal or an alkaline earth metal; more preferably, said salt is selected from the group comprising or, alternatively, consisting of sodium hyaluronate, potassium hyaluronate, calcium hyaluronate and magnesium hyaluronate.

RP6. The composition for use according to any one of the preceding RP1-RP5, wherein said salt is preferably sodium hyaluronate; more preferably, it is sodium hyaluronate having CAS no. 9067-32-7.

RP7. The composition for use according to any one of the preceding RP1-RP6, wherein said chondroitin, or a salt thereof, is preferably a chondroitin or a chondroitin sulphate or a chondroitin sulphate sodium selected from the group comprising or, alternatively, consisting of chondroitin of animal origin, preferably extracted from chickens, bovines or swine, or of another origin, e.g. fish or crustaceans, extracted from crabs, lobsters or prawn shells.

RP8. The composition for use according to RP7, wherein said chondroitin, or a salt thereof, preferably has an average molecular weight comprised from about 200 KDa to about 800 KDa; more preferably, said chondroitin, or a salt thereof, has an average molecular weight comprised from about 400 KDa to about 600 KDa.

RP9. The composition for use according to any one of the RP1, RP7 or RP8, wherein said chondroitin is preferably a chondroitin sulphate; more preferably, said chondroitin sulphate is at least 90% chicken chondroitin sulphate sodium.

RP10. The composition for use according to RP1, wherein said mixture may further comprise a basic substance with antacid properties; said basic substance with antacid properties is preferably a substance selected from the group comprising or, alternatively, consisting of a salt in the form of an oxide, a hydroxide, a carbonate, a bicarbonate, a silicate, a trisilicate, a sulphate or a citrate of a cation of an alkali metal or a cation of an alkaline earth metal or a cation of a metal (III).

R10b. A composition for use according to RP10, wherein said solid form of a chewable and/or suckable and/or melt-in-mouth and/or orally dissolving tablet, or the like, has the function of causing the dissolution of said hyaluronic acid, or a salt thereof, and said chondroitin, or a salt thereof and said basic substance with antacid properties in the saliva of the subject to whom said composition is administered so as to form a viscous gel that adheres to the mucosa of the various anatomical parts from the oral cavity to the stomach by swallowing of said gel.

RP11. The composition for use according to RP10, wherein said cation of an alkali metal or cation of an alkaline earth metal or cation of a metal (III) present in said salt is selected from the group comprising or, alternatively, consisting of: sodium cation, potassium cation, calcium cation, magnesium cation or aluminium cation; said cation of an alkaline earth metal is preferably the magnesium cation.

RP12. The composition for use according to either of the RP10 or RP11, wherein said salt is selected from the group comprising or, alternatively, consisting of aluminium hydroxide, magnesium hydroxide, or magnesium trisilicate, or mixtures thereof; said salt is preferably magnesium trisilicate, also in a hydrate form, such as, for example CAS no. 14987-04-3 (EINECS no. 239-076-7); said salt is preferably aluminium hydroxide on its own or aluminium hydroxide and sodium bicarbonate in a 2:1 ratio by weight; or magnesium hydroxide on its own or magnesium hydroxide and sodium bicarbonate in a 2:1 ratio by weight; or magnesium trisilicate on its own or magnesium trisilicate and sodium bicarbonate in a 2:1 ratio by weight.

RP12b. The composition for use according to either RP10 or RP11, wherein said salt, as a basic substance with antacid properties, is selected from the group comprising or, alternatively, consisting of: magnesium hydroxide, magnesium trisilicate and mixtures thereof; said salt is preferably magnesium trisilicate or magnesium trisilicate in a hydrate form, preferably magnesium trisilicate hydrate having the CAS no. 14987-04-3 (EINECS no. 239-076-7); or magnesium hydroxide on its own or magnesium hydroxide and sodium bicarbonate in a 2:1 ratio by weight; or magnesium trisilicate on its own or magnesium trisilicate and sodium bicarbonate in a 2:1 ratio by weight.

RP13. The composition for use according to any one of the preceding RP1-RP12, wherein said mixture may also further comprise a proton pump inhibitor compound—PPI; said proton pump inhibitor compound is preferably selected from the group comprising or, alternatively, consisting of: omeprazole, lansoprazole, esomeprazole, pantoprazole, rabeprazole sodium, ilaprazole or tenatoprazole.

R13b. A composition for use according to RP13, wherein said solid form of a chewable and/or suckable and/or melt-in-mouth and/or orally dissolving tablet, or the like, has the function of causing the dissolution of
said hyaluronic acid, or a salt thereof, and
said chondroitin, or a salt thereof and
said basic substance with antacid properties and
said proton pump inhibitor compound—PPI
in the saliva of the subject to whom said composition is administered so as to form a viscous gel that adheres to the mucosa of the various anatomical parts from the oral cavity to the stomach by swallowing of said gel.

RP14. The composition according to any one of the preceding RP1-RP13, wherein said mixture is present in said composition preferably in an amount comprised from 10% by weight to 80% by weight, relative to the final weight of the composition; more preferably, said mixture is present in said composition in an amount comprised from 30% by weight to 60% by weight, relative to the final weight of the composition.

RP15. The composition according to any one of the preceding RP1-RP14, wherein said mixture comprises or, alternatively, consists of:
a hyaluronic acid, or a salt thereof, in an amount comprised from 0.1% by weight to 5% by weight; preferably from 0.5% by weight to 2% by weight, relative to the total weight of the mixture;
a chondroitin, or a salt thereof, in an amount comprised from 20% by weight to 80% by weight; preferably from 30% by weight to 70% by weight, relative to the total weight of the mixture and, optionally;
an antacid substance in an amount comprised from 10% by weight to 50% by weight; preferably from 20% by weight to 40% by weight, relative to the total weight of the mixture and, optionally;
a proton pump inhibitor compound, in an amount comprised from 0.1% by weight to 10% by weight, relative to the total weight of the mixture; preferably from 0.5% by weight to 5% by weight, relative to the total weight of the mixture.

RP16. The composition for use according to any one of the preceding RP1-RP15, wherein said composition is for use:
i) in the treatment of subjects with disorders or symptoms caused or provoked by gastroesophageal reflux (GERD), or
ii) in the treatment of subjects with extraesophageal disorders or symptoms caused by the upflow of gastric contents and/or gastric vapours from the stomach along the oral cavity (also known as refluxate, which comprises pepsin, acid and mildly acidic or non-acidic but irritating contents), or
iii) in the treatment of subjects with ulcers or lacerations provoked in the gastric mucosa (stomach lining), in the esophageal and laryngopharyngeal mucosa or the tissues lining the oral cavity, so as to protect the mucosa and the tissues of the various anatomical regions from the damage provoked thereto;
wherein said subjects to be treated have proven to be non-responsive or poorly responsive to previous treatments carried out by administering alginates, such as sodium alginate or potassium alginate or magnesium alginate.

RP17. The composition for use according to any one of the preceding RP1-RP16, wherein said subjects belong to a subpopulation of patients diagnosed with GERD who have proven to be non-responsive or poorly responsive to previous treatments carried out by administering alginates, such as sodium alginate or potassium alginate or magnesium alginate.

RP18. The composition for use according to any one of the preceding RP1-RP17, wherein said composition is administered to subjects who also undergo a concomitant treatment with PPIs; the PPIs are preferably selected from the group comprising or, alternatively, consisting of: omeprazole, lansoprazole, esomeprazole, pantoprazole, rabeprazole sodium, ilaprazole or tenatoprazole.

RP19. The composition according to RP 18, wherein said subjects belong to a subpopulation of patients diagnosed with GERD who are treated with PPIs.

In a preferred embodiment, when the composition for use in a treatment method according to any one of the embodiments RP1-RP12(b) and RP14-RP19 is in the solid chewable form and comprises hyaluronic acid and chondroitin sulphate, said composition does not comprise aluminium hydroxide as a salt, i.e. as a basic substance with antacid properties.

In the context of the present invention, the proton pump inhibitor PPI selected from the group comprising or, alternatively, consisting of: omeprazole, lansoprazole, esomeprazole, pantoprazole, rabeprazole sodium, ilaprazole and tenatoprazole can be administered to patients both together with the compounds or substances (i), (ii) and, optionally, (iii) which make up the mixture contained in the composition of the present invention (all in the same mixture) or, alternatively, they can be administered separately from the composition of the present invention, for example in the form of a separate tablet of omeprazole (separate administration). Moreover, in the latter case, of separate administration, the administration can be deferred over time or concomitant, at the same moment. For example, two separate tablets, for example a first tablet of omeprazole, and then immediately a second tablet of the composition of the present invention.

Further preferred embodiments of the present invention Rn are set forth below.

R1. A composition for oral use in the solid form of a chewable and/or suckable and/or melt-in-mouth and/or orally dissolving tablet, preferably a suckable and/or melt-in-mouth and/or orally dissolving tablet, comprising a mixture which comprises or, alternatively, consists of:
a hyaluronic acid, or a salt thereof, and
a chondroitin, or a salt thereof and, optionally,
a basic substance with antacid properties selected from the group comprising or, alternatively, consisting of a salt in the form of an oxide, a hydroxide, a carbonate, a bicarbonate, a silicate, a trisilicate, a sulphate or a citrate of a cation of an alkali metal or a cation of an alkaline earth metal or a cation of a metal (III) and, optionally,
a proton pump inhibitor compound—PPI selected from the group comprising or, alternatively, consisting of: omeprazole, lansoprazole, esomeprazole, pantoprazole, rabeprazole sodium, ilaprazole and tenatoprazole and, optionally, at least one food or pharmaceutical grade excipient or additive; said composition being for use:

i) in the treatment of subjects with disorders or symptoms caused or provoked by gastroesophageal reflux (GERD), or ii) in the treatment of subjects with extraesophageal disorders or symptoms caused by the upflow of gastric contents and/or gastric vapours from the stomach along the oral cavity (also known as refluxate, which comprises pepsin, acid and/or mildly acidic or non-acidic but irritating contents), or iii) in the treatment of subjects with ulcers or lacerations provoked in the gastric mucosa (stomach lining), in the esophageal and laryngopharyngeal mucosa or the tissues lining the oral cavity, so as to protect the mucosa and the tissues of the various anatomical regions from the damage provoked thereto;

wherein said subjects to be treated have proven to be non-responsive or poorly responsive to previous treatments carried out by administering alginates, such as sodium alginate or potassium alginate or magnesium alginate.

RP1b. A composition for use according to RP1, wherein said solid form of a chewable and/or suckable and/or melt-in-mouth and/or orally dissolving tablet, or the like, has the function of causing the dissolution of said hyaluronic acid, or a salt thereof, and said chondroitin, or a salt thereof and, optionally, a basic substance with antacid properties and, optionally, a proton pump inhibitor compound—PPI in the saliva of the subject to whom said composition is administered so as to form a viscous gel that adheres to the mucosa of the various anatomical parts from the oral cavity to the stomach by swallowing of said gel.

R2. A composition for use according to R1 or R1b, wherein said hyaluronic acid, or a salt thereof, and said chondroitin, or a salt thereof, preferably both have an average molecular weight comprised from greater than about 1 KDa to less than about 1,000 KDa.

R3. The composition for use according to R1, R1b or R2, wherein said hyaluronic acid is preferably a linear, branched, cross-linked or substituted hyaluronic acid having an average molecular weight comprised from about 200 KDa to about 800 KDa; more preferably, said linear, branched, cross-linked or substituted hyaluronic acid has an average molecular weight comprised from about 400 KDa to about 600 KDa.

R4. The composition for use according to any one of the preceding R1-R3, wherein said hyaluronic acid is preferably the hyaluronic acid CAS no. 9004-61-9.

R5. The composition for use according to any one of the preceding R1-R4, wherein said hyaluronic acid is preferably in the form of a salt, such as a hyaluronate of an alkali metal or an alkaline earth metal; more preferably, said salt is selected from the group comprising or, alternatively, consisting of sodium hyaluronate, potassium hyaluronate, calcium hyaluronate and magnesium hyaluronate.

R6. The composition for use according to any one of the preceding R1-R5, wherein said salt is preferably sodium hyaluronate; more preferably, it is sodium hyaluronate having CAS no. 9067-32-7.

R7. The composition for use according to any one of the preceding R1-R6, wherein said chondroitin, or a salt thereof, is preferably a chondroitin or a chondroitin sulphate or a chondroitin sulphate sodium selected from the group comprising or, alternatively, consisting of chondroitin of animal origin, preferably extracted from chickens, bovines or swine, or of another origin, e.g. fish or crustaceans, extracted from crabs, lobsters or prawn shells.

R8. The composition for use according to R7, wherein said chondroitin, or a salt thereof, preferably has an average molecular weight comprised from about 200 KDa to about 800 KDa; more preferably, said chondroitin, or a salt thereof, has an average molecular weight comprised from about 400 KDa to about 600 KDa.

R9. The composition for use according to any one of the preceding R1-R8, wherein said chondroitin is preferably a chondroitin sulphate; more preferably, said chondroitin sulphate is at least 90% chicken chondroitin sulphate sodium.

R10. The composition for use according to R1, wherein said cation present in said salt is an alkali metal, or an alkaline earth metal, or a metal (III) and is selected from the group comprising or, alternatively, consisting of: sodium cation, potassium cation, calcium cation, magnesium cation or aluminium cation; said cation of an alkaline earth metal is preferably the magnesium cation.

R11. The composition for use according to the preceding R1 and R10, wherein said salt is selected from the group comprising or, alternatively, consisting of aluminium hydroxide, magnesium hydroxide, or magnesium trisilicate, or mixtures thereof; said salt is preferably magnesium trisilicate, also in a hydrate form, such as, for example, CAS no. 14987-04-3 (EINECS no. 239-076-7); said salt is preferably aluminium hydroxide on its own or aluminium hydroxide and sodium bicarbonate in a 2:1 ratio by weight; or magnesium hydroxide on its own or magnesium hydroxide and sodium bicarbonate in a 2:1 ratio by weight; or magnesium trisilicate on its own or magnesium trisilicate and sodium bicarbonate in a 2:1 ratio by weight.

R11b. The composition for use according to either of the embodiments R1 or R10, wherein said salt, as a basic substance with antacid properties, is selected from the group comprising or, alternatively, consisting of: magnesium hydroxide, magnesium trisilicate and mixtures thereof; preferably said salt is magnesium trisilicate or magnesium trisilicate in a hydrate form, preferably magnesium trisilicate hydrate having the CAS no. 14987-04-3 (EINECS no. 239-076-7); or magnesium hydroxide on its own or magnesium hydroxide and sodium bicarbonate in a 2:1 ratio by weight; or magnesium trisilicate on its own or magnesium trisilicate and sodium bicarbonate in a 2:1 ratio by weight.

R12. The composition according to R1, wherein said mixture is present in said composition preferably in an amount comprised from 10% by weight to 80% by weight, relative to the final weight of the composition; more preferably, said mixture is present in said composition in an amount comprised from 30% by weight to 60% by weight, relative to the final weight of the composition.

R13. The composition according to R1 and R12, wherein said mixture comprises or, alternatively, consists of:

a hyaluronic acid, or a salt thereof, in an amount comprised from 0.1% by weight to 5% by weight; preferably from 0.5% by weight to 2% by weight, relative to the total weight of the mixture;

a chondroitin, or a salt thereof, in an amount comprised from 20% by weight to 80% by weight; preferably from 30% by weight to 70% by weight, relative to the total weight of the mixture and, optionally;

an antacid substance in an amount comprised from 10% by weight to 50% by weight; preferably from 20% by weight to 40% by weight, relative to the total weight of the mixture and, optionally;

a proton pump inhibitor compound, in an amount comprised from 0.1% by weight to 10% by weight, relative to the total weight of the mixture; preferably from 0.5% by weight to 5% by weight, relative to the total weight of the mixture.

R14. The composition for use according to R1, wherein said subjects belong to a subpopulation of patients diagnosed with GERD who have proven to be non-responsive or poorly responsive to previous treatments carried out by administering alginates, such as sodium alginate or potassium alginate or magnesium alginate.

R15. The composition for use according to R1 and R14, wherein said composition is administered to subjects who also undergo a concomitant treatment with PPIs; preferably the PPIs are selected from the group comprising or, alternatively, consisting of: omeprazole, lansoprazole, esomeprazole, pantoprazole, rabeprazole sodium, ilaprazole and tenatoprazole.

R16. The composition according to R1, R14 and R15, wherein said subjects belong to a subpopulation of patients diagnosed with GERD who are treated with PPIs.

In a preferred embodiment, when the composition for use in a treatment method according to any one of the embodiments R1-R16 is in a chewable solid form and comprises hyaluronic acid and chondroitin sulphate, but does not also comprise a proton pump inhibitor (PPI), said composition does not comprise aluminium hydroxide as a salt, i.e. as a basic substance with antacid properties.

The composition for use according to the present invention can comprise, in addition to (i), (ii) and optionally (iii) and optionally (iv), at least one food or pharmaceutical grade excipient or additive among those that are commonly used and known to the person skilled in the art.

"Excipient or additive" (or inert ingredient) means any substance, or combination of substances, auxiliary to the production of a pharmaceutical, dietary or nutraceutical form, which is to be found in the finished product and is not the active ingredient, although it can modify the stability, release or other characteristics thereof. Non-limiting examples of such "excipients or additives", as known to the person skilled in the art of formulations in the pharmaceutical, nutraceutical or food sectors, are excipients such as diluents, absorbents, adsorbents, lubricants, glidants, colourants, surfactants, antioxidants, sweeteners, flavourings, binders, disintegrating agents, plasticisers, viscosity enhancing agents, emulsifiers, humectants, wetting agents, preservatives, chelating agents and the like.

As demonstrated in the in vivo studies reported in Experimental Parts (I) and (II), the compositions according to the invention (hyaluronic acid and chondroitin sulphate) for oral use in the monolithic solid form of chewable and/or suckable and/or melt-in-mouth and/or orally dissolving tablets, or the like, is capable of treating and/or significantly reducing gastroesophageal and extraesophageal reflux symptoms or disorders. In particular, composition C1 according to the invention (corresponding to the commercial product GERD-OFF®) is capable of treating and/or significantly reducing the number of heartburn episodes per week, with or without a concomitant treatment with PPIs, in patients who did not respond or only partially responded to treatments with alginates (Experimental Part (I)). Moreover, composition C1 according to the invention (corresponding to the commercial product GERDOFF®) administered in combination with a concomitant treatment with a proton pump inhibitor (PPI, omeprazole) showed a superiority of effectiveness against upper symptoms in patients who at the first diagnosis presented with extraesophageal symptoms associated with gastroesophageal reflux disease (GERD) compared to treatment solely with a proton pump inhibitor (Experimental Part (II).

As demonstrated, moreover, in the in vitro studies reported in Experimental Part (III), composition A according to the invention (corresponding to the commercial product GERDOFF®) for oral use in a monolithic solid form of chewable and/or suckable and/or melt-in-mouth tablets, or the like, has a better film-forming/mucoadhesive/protective action than the commercial compositions in a solid or gel form (B and C) it was compared to. At the same time, the composition according to the invention (A), as well as the compositions it was compared to (B and C), has a neutral impact on the integrity of the membrane epithelium.

Experimental Part (I)

The Applicant has tested 4 compositions, C1 (commercial product Gerdoff®), C2, C3 and C4 (Table 1) of the present invention with the aim of assessing their effects in patients with symptoms associated with GERD who are non-responsive or poorly responsive to treatments with alginates.

TABLE 1

| Qualitative-quantitative composition | | | | |
|---|---|---|---|---|
| Active components/ ingredients | mg/tab C1 (Gerdoff®), | mg/tab C2 | mg/tab C3 | mg/tab C4 |
| Chicken chondroitin sulphate sodium (ii) | 400 | 400 | 400 | 400 |
| Sucrose | 255 | 255 | 255 | 455 |
| Basic substance with antacid properties (iii) | Aluminium Hydroxide 200 | Magnesium trisilicate 200 | Mg(OH)$_2$ 200 | — |
| Calcium Carbonate | 100 | 100 | 100 | 100 |
| Liquorice flavouring | 70 | 70 | 70 | 70 |
| Glyceryl-Dibehenate (E471) | 20 | 20 | 20 | 20 |
| Silicon dioxide | 15 | 15 | 15 | 15 |

TABLE 1-continued

| Qualitative-quantitative composition | | | | |
| --- | --- | --- | --- | --- |
| Active components/ ingredients | mg/tab C1 (Gerdoff ®), | mg/tab C2 | mg/tab C3 | mg/tab C4 |
| Sodium Hyaluronate (i) | 10 | 10 | 15 | 15 |
| Ammonium Glycyrrhizate | 10 | 10 | 10 | 10 |
| Total weight | | 1100 mg | | |
| Pharmaceutical form | Melt-in-mouth or orally dissolving tablet, oval format 19 mm | | | |

For the sake of simplicity, only the results of the study conducted with composition C1 are reported. Results similar to those for composition C1 were also obtained with the other compositions C2, C3 and C4.

Reported here, in particular, are the results of an open-label clinical study conducted in two Italian centres with the aim of investigating the effect of a composition C1 in patients with symptoms associated with GERD who were non-responsive or poorly responsive to treatments with alginates.

The patients enrolled had a clinical diagnosis of GERD, had undergone treatment with alginates and/or alginic acid and/or any salt of the aforesaid alginic acid, such as, solely by way of example, but not exclusively, of sodium (sodium alginate), magnesium (magnesium alginate), or potassium (potassium alginate) and/or any biopolymer derived from algae and not only, having the same function as the above-mentioned alginate, for 2 weeks prior to enrolment, and presented with the following symptoms:

symptoms of heartburn and/or regurgitation of moderate intensity at least 2 times a week, for at least 2 weeks prior to enrolment which disturbed the patients during normal activities and/or in sleep recovery during the night;

symptoms representing at least one episode of heartburn per day for at least 4 days, not necessarily consecutive, during the week prior to enrolment.

In the context of this invention the patients as defined above are patients with a clinical diagnosis of GERD that is "non-responsive or poorly responsive to treatment with alginates".

Furthermore, the patients enrolled had to meet the following criteria:

submit a medical report relating to an esophagogastroduodenoscopy performed on the patient within 3 weeks before the start of the study, to rule out other severe pathologies affecting the upper gastrointestinal tract (e.g. gastric ulcers or duodenal ulcers);

have had a clinical response to a previous treatment with a PPI (e.g. omeprazole) at a stable dose within the 6 months prior to enrolment (therapy followed for at least 8 weeks).

The following were considered criteria for exclusion from the present clinical study:

the presence of esophagitis caused by infections or acidic/alkaline substances;

a treatment to eradicate *Helicobacter pylori* during the 30 days prior to enrolment;

Zollinger-Ellison syndrome;

a hiatal hernia;

Barrett's esophagus and the various types of diabetes.

The clinical study was approved by the local ethics committee (University Hospital and Polyclinic of Modena, International Ethics Committee Area A Milan) and conducted in accordance with the Helsinki Declaration (2013).

All of the patients gave their informed consent to participate in the study. The present clinical study was notified to the Italian Ministry of Health.

After signing the informed consent form, the patients underwent a baseline examination (V0) when a GERD patient history was drawn up and demographic details, information regarding lifestyle and dietary habits and medical data on vital parameters (heartrate, blood pressure, respiratory rate, weight, height, body-mass index) were collected. During this examination, a copy of the GIS (GERD Impact Scale) questionnaire and the daily diary were presented to patients and illustrated in detail. Patients were asked to complete the GIS questionnaire after 7 and 14 days of treatment. After 14 days, the patients underwent an end-of-study examination (V1) and returned both the questionnaire and the diary.

Patients were instructed to take 4 melt-in-mouth tablets containing chondroitin sulphate, aluminium hydroxide and hyaluronic acid with an average molecular weight comprised from 600 KDa to 800 KDa (C1 1100 mg) after meals and before going to bed for 14 days. The patients could take up to 6 tablets a day if the symptoms persisted.

A concomitant therapy with a PPI, such as omeprazole, lansoprazole, esomeprazole, pantoprazole, rabeprazole or other PPIs was allowed (the PPI allowed in this study was omeprazole in the majority of cases) during the study only if it had been maintained at stable doses during the two weeks prior to enrolment. Therefore, a recent or non-stable therapy with PPIs, intake of alginates and administration of H2 blockers, prokinetics, antacids or any product indicated for the treatment of GERD were not allowed for the entire duration of the study.

The primary endpoint consisted in a reduction in the number of episodes of heartburn one week after 14 days of treatment with the composition C1, compared to the baseline. The frequency of GERD-related symptoms after 7 and 14 days, patient satisfaction, the number of days without symptoms and patient compliance with the therapy were assessed as secondary endpoints in the GIS questionnaire and daily diary. Any symptom or event not directly correlated with GERD and variations in vital parameters during the study were recorded in the safety analysis.

All patients who had taken at least one treatment dose were included in the Intention-To-Treat (ITT) population and were also considered in the safety analysis. Patients without serious violations who received at least 80% of the C1 tablets to which the study related were included in the Per Protocol population (PP). Patients who received at least 80% of the C1 tablets to which the study related were defined as compliant with the treatment.

Although a formal calculation of the sample size is not necessary for explorative studies, we estimated that 33 patients would be sufficient to observe a reduction of at least 1 day per week in heartburn symptoms compared to the baseline, with a standard deviation of 2 days, a power of 80% for a two-tailed inferential test and a 0.05 probability that this was correct.

The continuous variables were recorded as the mean and standard deviation or median and range; the confidence limits considered were 95% of the mean. The baseline data were compared by means of a Student's paired samples t-test. The data originating from the GIS questionnaire were compared using a Student's paired samples t-test; each item was presented with the most suitable summary of the statistics; the number of days without symptoms was compared by means of a paired samples Wilcoxon test. A multivariate regression analysis was carried out to identify the items of the GIS questionnaire which mainly influenced the primary endpoint. All of the statistical analyses were conducted using PSPP (psppire.exe 0.8.3-g5f5de6, Free Software Foundation, http://www.gnu.org/software/pspp/).

Results

Baseline Characteristics

Forty patients were included in the study: thirty-nine patients were included in the ITT population, as one patient withdrew the informed consent without taking any treatment dose; thirty-six patients were included in the PP population, as one patient withdrew the informed consent after beginning treatment, one did not adhere to the treatment and one complained of headache and peaks of hypertension, not correlated with the C1 tablets that were the subject of the study, in addition to the patient already excluded from the ITT. The majority of patients were women (75%) and the mean age was 51.7 years (Table 2); the patients were married (69.2%), workers (62.5%) or retirees (30%) and 20% were smokers.

TABLE 2

| Variables | N = 40 |
|---|---|
| Age | 51.7 (17.0) |
| Females | 30 (75%) |
| Height (cm) | 164.8 (7.9) |
| BMI | 25.3 (4.8) |
| Smokers | 8 (20%) |
| Systolic pressure (mmHg) | 120.8 (10.4) |
| Diastolic pressure (mmHg) | 73.8 (8.2) |
| Heartrate (beats per minute) | 71.5 (7.4) |
| Respiratory rate (breaths per minute) * | 15.4 (1.2) |
| GERD symptoms | |
| Daily frequency | 1.9 (0.97) |
| Weekly frequency | 5.6 (2.99) |
| Severity of the symptoms | 6.9 (1.3) |
| PPI therapy initiated prior to the start of the study | 26 (65%) |

Both daily (1.9±0.97) and weekly (5.6±2.99) frequencies of GERD symptoms—heartburn, pain, reflux, coughing and other extraesophageal symptoms were recorded; the average intensity of the symptoms was 6.9±1.3. A stable therapy with PPIs had been undertaken by 26 (65.0%) patients, who were able to continue this treatment during the study (Table 2).

Primary endpoint: reduction in the number of heartburn episodes one week after 14 days of treatment with C1 and patient compliance The treatment with the composition C1 significantly reduced the number of heartburn episodes a week from the examination V0 to the examination V1 (after 14 days of treatment), in both the ITT population (from 5.4 days±1.5 to 1.8 days±2.1) and PP population (from 5.6 days±1.3 to 1.9 days±2.1)—FIG. 1. The mean difference was 3.5 days±2.47 (p<0.0001) for the ITT population and 3.6 days±2.5 (p<0.0001) for the PP population. During the period of the study, the 39 patients included in the ITT analysis received 56 tablets on average (±14.03), with only one patient not adhering to the treatment. The significant reduction in the days with heartburn episodes was already evident during the first week (7 days) of treatment with C1 (p<0.0001 vs baseline)—FIG. 2 (referring to the ITT population).

Subgroup of patients with allowed concomitant treatment with PPIs.

In the two weeks prior to enrolment, 26/40 patients (25 in the population ITT and 23 in the PP population) were already using PPIs at a stable dose and they were thus able to continue taking PPIs in combination with C1 during the study. The average weekly frequency of heartburn in this subgroup of patients was 5.2 days at baseline, whereas following treatment with C1 it was reduced to 1.5 days a week (in the last week after 14 days of treatment). The number of days with heartburn episodes was also significantly reduced during the first week (7 days) of treatment with C1 in both the ITT (1.8 d/w±2.0 d/w) and PP (2.0 d/w±2.0 d/w) populations and continued to decrease slightly during the second week of treatment (FIG. 3).

Subgroup of Patients without Concomitant Treatment with PPIs

Among the remaining 14 patients who did not use PPIs at a stable dose during the study, the average number of days with heartburn at baseline was 5.7 per week. In these patients, C1 reduced this frequency to an average of 2.21 days per week (in the last week after 14 days of treatment). The number of days with heartburn episodes was also significantly reduced during the first week (7 days) of treatment with C1 in both the ITT (2.5 d/w±2.0 d/w) and PP (2.7 d/w±2.0 d/w) populations and continued to decrease slightly during the second week of treatment (FIG. 3).

Primary Endpoint: Results of the GIS Questionnaire and Patient Satisfaction

The results of the GIS questionnaire are shown in detail in Table 3.

TABLE 3

| | | Baseline examination (V0) | Final examination (V1) | p |
|---|---|---|---|---|
| How often did you have pain in your chest or behind your breastbone? | Never | 27.5 | 59.0 | 0.0183 |
| | Every day | 5 | 0.0 | |
| | Sometimes | 45 | 38.5 | |
| | Often | 22.5 | 2.6 | |
| How often did you have a burning sensation in your chest or behind your breastbone? | Never | 15 | 61.5 | 0.0103 |
| | Every day | 15 | 0.0 | |
| | Sometimes | 42.5 | 35.9 | |
| | Often | 27.5 | 2.6 | |

TABLE 3-continued

| | | Baseline examination (V0) | Final examination (V1) | p |
|---|---|---|---|---|
| How often did you have | Never | 12.8 | 51.28 | 0.3778 |
| regurgitation or a sour taste in your | Every day | 17.9 | 2.56 | |
| mouth? | Sometimes | 38.5 | 33.33 | |
| | Often | 30.8 | 12.82 | |
| How often did you have pain or | Never | 10.0 | 53.8 | 0.0102 |
| burning in the upper part of your | Every day | 17.5 | 0.0 | |
| stomach? | Sometimes | 32.5 | 46.2 | |
| | Often | 40.0 | 0.0 | |
| How often did you have sore throat | Never | 25.64 | 53.8 | 0.0555 |
| or hoarseness tied to heartburn or | Every day | 15.38 | 2.6 | |
| acid reflux? | Sometimes | 28.21 | 41.0 | |
| | Often | 30.77 | 2.6 | |
| How often did you have difficulty | Never | 22.5 | 61.5 | 0.0232 |
| in sleeping well at night because of | Every day | 2.5 | 0.0 | |
| your symptoms? | Sometimes | 50.0 | 30.8 | |
| | Often | 25.0 | 7.7 | |
| How often did you have symptoms | Never | 17.5 | 59.0 | 0.3755 |
| that prevented you from eating any | Every day | 12.5 | 0.0 | |
| type of food? | Sometimes | 40.0 | 25.6 | |
| | Often | 30.0 | 15.4 | |
| How often did you have symptoms | Never | 34.2 | 74.4 | 0.4319 |
| from the start of a working day or | Every day | 2.6 | 0.0 | |
| during everyday activities? | Sometimes | 60.5 | 23.0 | |
| | Often | 2.6 | 2.6 | |
| How often did you take additional | Never | 25.6 | 92.3 | 0.0509 |
| medicine other than the ones | Every day | 5.2 | 0.0 | |
| prescribed by the doctor? | Sometimes | 43.6 | 5.1 | |
| | Often | 25.6 | 2.6 | |

The treatment with C1 significantly reduced the frequency of the sensation of chest and breastbone pain or burning, pain or burning in the upper part of the stomach and sleep disturbances. A reduction was also observed, albeit not a statistically significant one, in the frequency of sore throat and hoarseness and in the administration of additional drugs (Table 3).

Furthermore, the GIS score decreased significantly from V0 to the intermediate time T7 (7 days of treatment) and from V0 to V1 (14 days of treatment) both in patients not treated with a PPI and patients treated with a concomitant therapy with a PPI (FIGS. 4 and 5) (details of the questionnaire not shown). All of the symptoms assessed in the GIS questionnaire (with the exception of the item "How often has your sleep been disturbed during the night because of your symptoms?" In the subgroup not treated with PPIs, p=0.0547) decreased significantly after the treatment with C1 and no differences were found between the patients treated with or without PPIs. It was reported that sore throat and hoarseness were present daily or often at V0 in 40% and 45.8% and at V1 in 6.6% and 4.2% of patients who were not treated or treated with PPIs, respectively.

The patients' opinions about the effect of C1 were assessed by the researchers during examination V1 using a satisfaction questionnaire. In the ITT population, 18 patients (46.2%) rated the treatment as very good and 17 patients (43.6%) as good, reaching a total of 35 patients (89.8%) extremely satisfied with the treatment.

A multivariate analysis indicated that the reduction in the number of episodes of heartburn was mainly correlated to the presence of "pain in the chest or behind the breastbone" and "regurgitation or sour taste in the mouth"; "pain or burning in the upper part of the stomach" and "burning sensation in the chest or behind the breastbone" had an over 10% probability of being relevant in influencing the number of episodes of heartburn.

DISCUSSION

This explorative study showed that a treatment of 14 days with a formulation of hyaluronic acid and sulphate of chondroitin C1 in the form of a melt-in-mouth tablet was able to significantly reduce the number of episodes of heartburn per week in patients that had not responded or had partially responded to alginates, also with a concomitant PPI therapy, as mentioned above. In particular, the reduction in the number of heartburn episodes per week in the first 7 days and last 7 days of the 14-day treatment with C1 did not differ between patients who were not treated with PPIs and patients treated with a concomitant therapy with PPIs.

Based on the patient's self-assessment, as recorded in the GIS questionnaire, C1 significantly reduced the sensation of pain and burning in the chest, pain or burning in the upper part of the stomach and sleep disturbances caused by the symptoms. Taking the C1 tablet considerably improved sore throat or hoarseness and reduced the use of additional drugs/treatments.

To the best of our knowledge, this was the first study conducted on patients with GERD who are non-responsive or poorly responsive to treatments with alginates, e.g. sodium, or magnesium, or potassium alginates. Our results suggest that a 14-day treatment with C1 demonstrated to be effective in reducing the typical symptoms of GERD (for example heartburn) in this group of patients and showed a positive, albeit non statistically significant, action on atypical symptoms (for example sore throat or hoarseness). Furthermore, the GIS questionnaire was used to specifically examine the experience of patients with GERD symptoms and their impact on everyday life. Among GERD symptoms, heartburn considerably impacts everyday life, causing greater sleep interruptions, greater difficulty in drinking and eating and lower general health scores. Therefore, the reduction in the episodes of heartburn per week obtained with C1 could favourably impact patients' quality of life, as shown by the GIS results.

A stable pre-treatment with PPIs was observed in the majority of patients, but the GERD symptoms at baseline were similarly present in all patients. PPIs represent the treatment of choice for GERD, but approximately 30% of patients with GERD continue to have symptoms with the administration once a day of the standard PPI doses. Concomitant treatment with the composition C1 and PPIs reduced GERD symptoms in a manner similar to what occurs in patients who received only C1. Therefore, C1 has shown an effect complementary to that of PPIs and significantly improved the therapeutic outcomes.

We can conclude that the 14-day treatment with the composition of the present invention C1 in the form of a chewable and/or suckable and/or melt-in-mouth tablet significantly reduced the GERD symptoms in patients who are non-responsive or poorly responsive to treatments with formulations containing alginates. The clinical improvement was also observed with a stable, concomitant treatment with PPIs. The composition of the present invention has also demonstrated to be safe and well tolerated, as indicated by the high degree of satisfaction shown by patients.

Experimental Part (II)

The Applicant conducted the following multi-centre prospective, randomised, open-label clinical study, with two parallel arms of treatment, in order to assess the effect of a composition C1, C2, C3 and C4 (according to Table 1) in combination with a concomitant treatment with proton pump inhibitors—PPIs (omeprazole), versus the treatment with proton pump inhibitors—PPIs (omeprazole) alone, administered for 6 weeks, on the upper symptoms associated with GERD, in patients with a first diagnosis of gastroesophageal reflux disease. For the sake of simplicity, only the details of the study conducted with C1 (commercial product GERD-OFF®) are reported.

The aim of the present study was to assess, in patients who, at the first diagnosis, presented with extraesophageal symptoms associated with gastroesophageal reflux disease (GERD), the effect of a 6-week treatment with the composition C1 comprising a chondroitin sulphate, a hyaluronic acid or a salt thereof and an aluminium hydroxide, in combination with a treatment with proton pump inhibitors (PPI) versus treatment with PPIs alone; i.e. to verify the reduction in the frequency of symptoms in patients by means of the Likert questionnaire, and the severity of upper symptoms, by means of the RSI (Reflux Symptom Index) questionnaire, and to assess Responders and Non-Responders in the two groups of patients after 6 weeks of treatment versus the baseline.

Furthermore, the maintenance of the effect of the combined treatment (C1+PPIs) on extraesophageal symptoms was assessed after a follow-up period (FU) lasting 12 weeks, which included only responder patients, defined as patients who at the 6th week of treatment had reached an RSI score at least 50% lower than the baseline and an absolute value of <13, enrolled in the C1+PPI treatment arm. The patients included in the FU period were randomly assigned to the C1 group or control group (no treatment).

The primary aim was to assess the improvement in upper symptoms with the association of PPIs+C1 (commercial product GERDOFF®) versus PPIs and the subsequent maintenance period.

The secondary objectives were to assess the following parameters in the treated patients:

- the number and percentage of Responders/Non-Responders at the examination V4, after 6 weeks of treatment with C1+PPIs/PPIs;
- the number and percentage of patients who had maintained the effect of the treatment at the final follow-up—FU examination (V6), versus the examination at the end of the study (V4); that is, after 12 weeks of treatment with C1 or no treatment (control group);
- the percentage of reduction in the frequency of symptoms, as per the Likert questionnaire, at the examination V4, after 6 weeks of treatment, versus the baseline and versus the two treatment groups;
- the percentage of reduction in the frequency of symptoms, as per the Likert questionnaire, at the examination V6 18 weeks after the start of treatment, versus V4 and versus the two treatment groups;
- overall patient's satisfaction with the treatment on a semi-quantitative ordinal scale during the treatment period;
- any concomitant use of other drugs/products not allowed, as specified below, used as "rescue medication" in order to keep the symptoms under control, during the first 6 weeks of treatment;
- any concomitant use of rescue medication, whether allowed or not, in the FU period;
- safety was assessed, in all patients included, by recording any variations in basic blood chemistry parameters and recording of adverse incidents/events that had occurred:
  - i) during the first 6 weeks of treatment, for the patients included in Group 2, with PPIs only, and Non-Responder patients included in Group 1, C1+PPIs; or
  - ii) during the whole of the study period, 18 weeks, for the patients who also continued with the FU period; or
  - iii) during the examinations V1, V4 and V6, the Beta-hCG levels were assessed only in women of childbearing age.

The multi-centre prospective, randomised, open-label clinical study, with two parallel arms of treatment, followed by the FU period, provided for the treatment, for 6 weeks, of 78 patients diagnosed for the first time, who presented with upper symptoms ascribable to a diagnosis of GERD, in the presence/absence of typical symptoms. The patients were thus randomly assigned, on an open-label basis, in a 1:1 ratio:

- 39 patients were treated with C1+PPIs (omeprazole) for 6 weeks; and
- 39 patients were treated only with a PPI (omeprazole) for 6 weeks.

Only the patients classified as Responders at examination V4 and belonging to the group C1+PPIs were included at the FU stage, which lasted 12 weeks. During the FU period, the patients were randomly assigned, on an open-label basis, in a 1:1 ratio to the C1 group (GERDOFF®) or the control group, which received no treatment for 12 weeks, in order to assess whether the effect of the associated treatments had been maintained. Safety was assessed in all patients included in the study up to V4, and up to V6 in patients who continued with the FU period.

Six examinations were planned during the study:

- T0: baseline examination V1 at day 0;
- T1: check-up examination V2 after 1 week±1 day;
- T3: check-up examination V3 after 3 weeks±2 days;
- T6: end-of-study examination V4 after 6 weeks±2 days and starting examination of the FU period for the Responder patients of Group 1;

T12: follow-up examination FU V5 after 12 weeks±3 days;

T18: final examination FU V6 after 18 weeks±3 days.

Some intermediate examinations were planned: one after 1 week of treatment (V2) and one after 3 weeks of treatment (V3), in order to assess the trend in the response to the treatment, and, finally, another end-of-study examination (V4) after 6 weeks of treatment to verify state of health and the effect of the treatment taken.

On these occasions patients filled out the RSI questionnaire, for the assessment of the severity of symptoms, and the Likert scale, for the assessment of the reduction in the frequency of symptoms. At the end-of-study examination (V4), the patients were classified as Responders and Non-Responders. Patients belonging to the C1+PPIs group, who were judged as Responders at V4, were randomly assigned, on an open-label basis, in a 1:1 ratio, to receive C1/no treatment and continued with a 12-week FU period. Planned during that period were an intermediate examination (V5) after 6 weeks and a final examination (V6), during which an assessment was made of whether the effect of the treatment had been maintained. The questionnaire RSI was provided for the purpose of assessing the severity of the symptoms and to assess the reduction in the frequency of symptoms via the Likert scale. In this period, only the use of omeprazole (PPI), at a constant dosage, was allowed, according to the indications of the investigator, both to the patients included in the untreated group and in the treatment group, as a rescue medication to control symptoms and safety data were assessed. The use of no other drugs was allowed. During the final FU examination (V6), an assessment was also made of the degree to which the effect of the treatment was maintained on the upper symptoms specified in the RSI questionnaire.

The composition C1 (GERDOFF®—DM class III) comprises:

| | |
|---|---|
| chondroitin sulphate sodium salt | 400.00 mg |
| sucrose | 275.00 mg |
| aluminium hydroxide | 200.00 mg |
| calcium carbonate | 100.00 mg |
| anti-caking agents: mono-di-and tri-glycerides of fatty acids, silicon dioxide | 35.00 mg |
| Sodium Hyaluronate | 10.00 mg |
| flavouring | 70.00 mg |
| sweetener: ammonium glycyrrhizate | 10.00 mg |
| Orally chewable tablet with a weight equal to | 1,100 mg. |

Study Treatments

GROUP 1: C1 with a dosage of 1 tablet 3 times a day: 1 tablet after breakfast, 1 tablet after lunch, 1 tablet in the evening before going to bed, and Omeprazole oral tablets (PPI) with a dosage of 2 20 mg tablets once a day in the morning before breakfast.

Duration of the treatment: 6 weeks±2 days.

GROUP 2: Omeprazole oral tablets (PPI) with a dosage of 2 20 mg tablets once a day in the morning before breakfast.

Duration of the treatment: 6 weeks±2 days

Follow-up Period: during the 12-week-long FU period, which began starting from the end-of-study examination V4, the Responder patients belonging to Group 1 were randomly assigned to receive the treatment with C1, according to the dosage specified above, or to the control group, and thus untreated. Both groups of patients received a supply of Omeprazole (PPI), the only allowed rescue medication, to be taken only according to the indications of the investigator and at a constant dosage.

During the FU period (V4-V6), only in the event of a worsening of symptoms, the use of Omeprazole at a constant dosage as a rescue medication was allowed both to patients included in the control Group and patients included in the C1 Group.

Chronic use of drugs that interfere with salivary secretion (e.g. antihistamines or steroids for inhalation) and the previous use of PPIs and/or medical devices and/or analogous products (e.g. alginates, antacids, etc.) was not allowed in the 4 weeks prior to inclusion in the study.

During the first period of treatment, lasting 6 weeks, it was not permitted to take any other type of drug. During the FU period, only the use of Omeprazole (PPI) at a constant dosage was allowed, only if necessary and according to the indications of the investigator, as a rescue medication and the adoption of no other therapy for GERD was allowed.

Inclusion Criteria
1. male or female subjects;
2. age ≥8 years;
3. first diagnosis of GERD with upper symptoms, clinically performed and confirmed by an ENT specialist and/or confirmed by a gastroenterologist by means of an RSI questionnaire;
4. presence of extraesophageal symptoms associated with GERD;
5. RSI value ≥20;
6. patients not pre-treated with PPIs, also for problems different from GERD, and/or with medical devices, and/or with similar products (e.g. alginates) in the past 4 weeks;
7. cooperative patients able to understand the study procedure and abide by it;
8. patients capable of freely giving their written informed consent to participation in the study;
9. patients who freely gave their consent to the processing of personal data related to the study.

Exclusion Criteria
1. known esophagitis due to infection or acid or alkaline substances;
2. acute or chronic rhinosinusitis;
3. chronic bronchitis;
4. known Zollinger-Ellison syndrome, hiatal hernia larger than 3 cm and Barrett's esophagus;
5. ongoing neoplasia;
6. uncontrolled diabetes;
7. patients with compromised liver function;
8. patients with rare hereditary problems of galactose intolerance;
9. patients who, in the investigator's view, cannot be included in the protocol also on the basis of other pathologies or concomitant therapies, such as, for example, the intake of atazanavir, nelfinavir, clopidogrel, posaconazole and erlotinib (as recommended in the SPC);
10. patients with Lapp lactase deficiency;
11. patients with Glu-Gal malabsorption syndrome;
12. patients with hypersensitivity to omeprazole, substituted benzimidazoles or any of the excipients;

13. patients already undergoing treatment with PPIs or analogous products;

14. chronic use of drugs that interfere with salivary secretion (e.g. antihistamines or steroids for inhalation);

15. drug and alcohol abuse;

16. inability of the subject to adequately express his or her ailments;

17. patients with planned or ascertained pregnancy or who do not adopt an accepted method of contraception;

18. patients who are breastfeeding;

19. failure to give consent to the processing of personal data.

The sample size was determined on the basis of hypotheses formulated in relation to the primary aim of the study, namely, to verify how the score associated with the Reflux Symptom Index (RSI) questionnaire, measured at baseline and after 6 weeks of treatment, varied differently in the two treatment groups, PPIs and PPIs+C1, so as to highlight that the addition of C1 more greatly favours both the effect of eliminating the upper symptoms and the rapidity with which the upper symptoms are controlled.

This effect was evaluated based on the variations in the mean value of RSI compared to the values upon inclusion in the study, taking into consideration the variables: age, standard deviations and expected value after treatment with Omeprazole (PPI). The assumptions used for the calculation were the following:

Difference between the two treatments (DELTA): 3.6

Standard deviation in relation to Delta: 5

On the basis of the stated assumptions, for a comparison based on an independent-sample Student's t test at a power of 80% and a 5% level of probability for a two-tailed test, 62 patients were included in the study (31 patients per treatment group). Applying a correction for a 20% drop-out rate, 78 patients would have to be included, 39 patients per treatment group.

In order to assess the effect of the study treatment, the following were analysed:

at the examination V4 (end of the first phase of the study), the variation versus the baseline value in the score of the RSI questionnaire in order to verify the effect of the treatments on the upper symptoms; (primary endpoint);

the reduction with respect to the frequency of symptoms, by means of the Likert scale;

the number and % of Responders/Non-Responders at the end-of-study examination (after 6 weeks of treatment);

the reduction in the frequency of symptoms, by means of the Likert scale at the end-of-study examination (after 6 weeks of treatment);

at baseline, the end-of-study examination (after 6 weeks of treatment) and FU examination (after 12 weeks of treatment), the presence of upper symptoms by means of the RSI questionnaire and Likert scale;

at the examinations V4 (end of study) and V6 (end of FU), the questionnaires regarding the trend in the upper symptoms (RSI questionnaire and Likert scale) in order to assess whether the effect was maintained;

non-control of symptoms during the first 6 weeks of treatment, and administration of rescue medication: therapy adopted, frequency of administration, time of administration and dose taken;

consumption of rescue medication according to need during the FU period: therapy adopted, frequency of administration, time of administration and dose taken.

All of the analyses were conducted in accordance with the intention-to-treat (ITT) principle as laid down in ICH-E9. The ITT population was defined as: "all patients randomly assigned in the first study period (first 6 weeks) who took at least one treatment dose". The ITT population coincides with the population that will be used for the safety analysis. This criterion is in accordance with ICH-E9 as excluding factors that may generate a bias in the assessment both of effectiveness and safety data.

The patients that could be assessed were all those who took at least 95% of the overall dose in the 6-week period. For the purpose of analysing the differences between groups, parametric or non-parametric tests were used after conducting a verification of the subtended distribution. All of the statistical analyses were performed using free statistical software. The significance level was fixed at 5% for a two-tailed test. In order to assess the effect of the treatment, the primary variable, represented by the difference in the RSI score measured after 6 weeks of treatment compared to the baseline, was taken into consideration. The two treatment groups were compared using the independent-sample Student's t test. The treatments were considered statistically different if both the probability value was lower than the pre-established threshold and the hypothesised DELTA value of 3.6 between the two treatments was reached. The patients who, at the 6th week of treatment, reached an RSI score at least 50% lower than the baseline and an absolute value <13 were defined Responders. For the comparison between Responders and Non-Responders in the two treatment groups, use was made of the Chi-squared test with Yates' correction or, depending on the number of subjects per group, Fisher's exact test.

The administration of any type of rescue medication in each treatment group during the first 6 weeks of the study was compared by means the Chi-squared test. The average dose of rescue medication in the two treatment groups during the 6-week period will be assessed by means of a non-parametric (distribution-free) Mann-Whitney U test. Analysis in the Follow-up (FU) period: effectiveness data were presented for the treatment groups exclusively using the descriptive statistics that were most appropriate and consistent with the actual sample size. The administration of rescue medication, both allowed and not allowed, during the FU period, in each treatment group was presented as a frequency and percentage.

Duration of the Study:

Enrolment period: approximately 9-12 months.

Duration of the treatment with C1 GERDOFF®+PPI/PPI: 6 weeks±2 days.

Duration of the follow-up treatment with C1 GERD-OFF®: 12 weeks±2 days.

FIG. 6 shows the duration of the clinical study.

Table 4 shows the flow chart of the clinical study.

TABLE 4

| | V1 Baseline | V2 (intermediate assessment) | V3 (intermediate assessment) | V4[a] End of study/early termination © Period | V5[b] FU (follow-up examination)[d] | V[b] End of FU/early termination[d] |
|---|---|---|---|---|---|---|
| | T0 | T1 1 week ± 1 day | T3 3 weeks ± 2 days | T6 6 weeks ± 2 days | T12 12 weeks ± 3 days | T18 18 weeks ± 3 days |
| Informed consent | X | | | | | |
| Inclusion/exclusion criteria | X | | | | | |
| Demographic data | X | | | | | |
| Vital signs | X | | | X | | X |
| First diagnosis of GERD of diagnosis confirmation | X | | | | | |
| Patient history | X | | | | | |
| Referred by: Ear, Nose and Throat specialist | X | | | | | |
| Objective examination and concomitant pathologies | X | | | X | | X |
| Assessment of symptoms | X | X | X | X | X | X |
| Blood chemistry tests | X | | | X | | X |
| Beta-hCG[(1)] | X | | | X | | X |
| Delivery of treatment with GERDOFF ®+ PPIs or PPIs | X | | | | | |
| Delivery of treatment with GERDOFF ®/no treatment and rescue[(2)] | | | | X | | |
| Concomitant therapies | X | X | X | X | X | X |
| Likert Scale | X | X | X | X | X | X |
| RSI questionnaire | X | X | X | X | X | X |
| Submission/collection of diaries | X | X | X | X | X | X |
| Questionnaire on satisfaction with treatment | | X | X | X | | |
| Assessment of Responders and Non-Responders | | | | X | | |
| Assessment of whether the effect was maintained | | | | | | X |
| Adverse events/incidents | | X | X | X | X | X |
| Assessment of compliance with GERDOFF ® + PPIs and product accounting | | | | X | | |
| Assessment of compliance with GERDOFF ® and product accounting | | | | | | X |
| Consumption of rescue medication | | X | X | X | X | X |
| End-of-study examination | | | | X | | |
| Examination at end of FU | | | | | | X |

During the study period, the patient was asked to fill out a diary to record the presence and intensity of the upper symptoms, in line with the questions listed in the RSI questionnaire, the consumption of rescue medication, according to need, during the first 6 weeks of treatment and the FU phase and any adverse events or incidents occurring during the study period.

(a) End-of-Study Examination for all patients included in the study. The Responder patients included in Group 1 (C1+PPIs) immediately continued the study with the FU phase.

(b) Only the Responder patients included in Group 1 (C1+PPIs) were included in the FU phase.

(1) Only in women of childbearing age.

(2) Only in Responder patients of Group 1 who participate in the FU phase.

(3) during the first 6 weeks, the use of any type of rescue medication was not allowed in either of the two treatment groups. During the FU phase it was permitted to use only Omeprazole (PPI), at a constant dosage and only if necessary, as a rescue medication in both groups of patients, untreated (control) and treated, whereas it was not permitted to use other products as rescue medication for the control of GERD. (c) premature termination of participation in the study was considered a "Treatment Failure".

Results
Primary Endpoint Results:

At the examination V4 (end of the first stage of the study after 6 weeks of treatment with C1+PPI or only the PPI) the variations compared to the baseline value (examination V1) in the score of the RSI questionnaire were recorded and analysed in order to verify the effect of the treatments on the upper symptoms (primary endpoint).

The preliminary results are shown in Table 5 (data for individual patients) and Table 6 (comparative data based on the total results of Table 5) as overall data of the studies carried out in two different experimental centres. A total of 72 patients were enrolled, but Table 5 refers to only 64 patients who met the inclusion and exclusion criteria of the study and who, at the time of the analysis, had already undergone the examination V4 for the primary endpoint.

These first data show a superiority of effectiveness against symptoms in Group 1 receiving composition C1 (GERD-OFF®) in combination with a concomitant treatment with a proton pump inhibitor PPI (omeprazole) (C1+PPI, GERD-OFF®+omeprazole) compared to Group 2 receiving a PPI (omeprazole) alone, even though the difference between the two groups is not statistically significant. A positive trend is observed from Table 5, with a difference in means equal to −2.38 between the two groups, in favour of Group 1 undergoing treatment with C1+PPI.

An assessment with respect to the other endpoints and the descriptive analysis are currently being drawn up.

Experimental Part (III)

The Applicant conducted in vitro studies to evaluate the film forming action on a model of human esophageal epithelium (film forming/mucoadhesive/protective action) and the effect on the integrity of the epithelium of a composition according to the invention compared with commercial products.

III.1) Effectiveness of Film Forming Action i) Study compositions and Controls negative control: saline solution (NC), positive control: white petroleum jelly (V).

composition A: commercial product GERDOFF® milk flavour (solid), composition of the present invention;

TABLE 5

| Subject | Treatment | RSI V1 | RSI V4 | DELTA | Subject | Treatment | RSI V1 | RSI V4 | DELTA |
|---|---|---|---|---|---|---|---|---|---|
| 101 | C1 + PPI | 28 | d-o | | 102 | PPI | 27 | 16 | 11 |
| 104 | C1 + PPI | 23 | 7 | −16 | 103 | PPI | 24 | 11 | −13 |
| 106 | C1 + PPI | 32 | 16 | −16 | 105 | PPI | 21 | 10 | −11 |
| 108 | C1 + PPI | 31 | 11 | −20 | 107 | PPI | 22 | 5 | 17 |
| 110 | C1 + PPI | 28 | 19 | −9 | 109 | PPI | 21 | 3 | −18 |
| 112 | C1 + PPI | 21 | 21 | 0 | 111 | PPI | 24 | 17 | −7 |
| 113 | C1 + PPI | 20 | 5 | −15 | 115 | PPI | 32 | 1 | −31 |
| 114 | C1 + PPI | 21 | 20 | 1 | 116 | PPI | 32 | 25 | −7 |
| 117 | C1 + PPI | 21 | 1 | −20 | 118 | PPI | 25 | 5 | −20 |
| 119 | C1 + PPI | 22 | 5 | −17 | 120 | PPI | 23 | 8 | −15 |
| 121 | C1 + PPI | 21 | 10 | −11 | 123 | PPI | 21 | 0 | −21 |
| 122 | C1 + PPI | 20 | 13 | 7 | 125 | PPI | 20 | 26 | 6 |
| 124 | C1 + PPI | 20 | 0 | 20 | 126 | PPI | 21 | 29 | 8 |
| 129 | C1 + PPI | 21 | 1 | −20 | 127 | PPI | 24 | 9 | −15 |
| 133 | C1 + PPI | 22 | 1 | −21 | 128 | PPI | 34 | 10 | −24 |
| 136 | C1 + PPI | 30 | 10 | −20 | 130 | PPI | 24 | 0 | −24 |
| 138 | C1 + PPI | 23 | 4 | −19 | 131 | PPI | 20 | 15 | 5 |
| 140 | C1 + PPI | 22 | 10 | 12 | 132 | PPI | 27 | 28 | 1 |
| 142 | C1 + PPI | 20 | 3 | −17 | 134 | PPI | 24 | 9 | −15 |
| 143 | C1 + PPI | 41 | 3 | −38 | 135 | PPI | 26 | 39 | 13 |
| 146 | C1 + PPI | 21 | 8 | −13 | 137 | PPI | 34 | 20 | −14 |
| 149 | C1 + PPI | 31 | 2 | −29 | 139 | PPI | 24 | 13 | −11 |
| 202 | C1 + PPI | 21 | 4 | −17 | 141 | IPPI | 24 | 13 | −11 |
| 204 | C1 + PPI | 23 | 3 | −20 | 144 | PPI | 23 | 16 | 7 |
| 206 | C1 + PPI | 22 | d-o | | 145 | PPI | 22 | 10 | −12 |
| 207 | C1 + PPI | 36 | 14 | −22 | 147 | PPI | 32 | 4 | −28 |
| 208 | C1 + PPI | 22 | 3 | −19 | 148 | PPI | 37 | 18 | −19 |
| 211 | C1 + PPI | 20 | 12 | −8 | 201 | PPI | 31 | d-o | |
| 213 | C1 + PPI | 23 | 7 | −16 | 203 | PPI | 27 | 16 | −11 |
| 214 | C1 + PPI | 21 | d-o | | 205 | PPI | 33 | 6 | −27 |
| 215 | C1 + PPI | 29 | d-o | | 209 | PPI | 33 | 4 | −29 |
| 218 | C1 + PPI | 23 | 16 | −7 | 210 | PPI | 35 | 1 | −34 |
| | | | | | 212 | PPI | 20 | 16 | −4 |
| | | | | | 216 | PPI | 28 | 12 | −16 |
| | | | | | 217 | PPI | 27 | 4 | −23 |
| | | | | | 219 | PPI | 24 | 15 | −9 |
| | | | | | 220 | PPI | 21 | 9 | −12 |
| N | 28 | | | | N | 36 | | | |
| MEAN | −16.07 | | | | MEAN | −13.69 | | | |
| SD | 7.79 | | | | SD | 10.61 | | | |
| STDERR | 1.47 | | | | STDERR | 1.77 | | | | d-o: drop-out patient

TABLE 6

| | |
|---|---|
| PROBABILITY LEVEL | 0.05 |
| CODE TEST | 2 |
| MEAN OF TREATMENT WITH C1 + PPI | −16.07 |
| MEAN OF TREATMENT WITH PPI | −13.69 |
| DIFFERENCE BETWEEN MEANS | −2.38 |
| POOLED STANDARD DEVIATION | 9.2 |
| EFFECT SIZE | 0.259 |
| TEST POWER (%) | 17 |
| NUMBER OF PATIENTS C1 + PPI | 28 |
| NUMBER OF PATIENTS PPI | 36 |
| TOTAL NUMBER OF PATIENTS | 64 | composition B: commercial product NEOBI-ANACID® (solid), comparative composition;

composition C: commercial product MARIAL GEL® (liquid), comparative composition.

Composition A (GERDOFF® milk flavour) comprises the ingredients as defined in Table 1 for composition C1.

Composition B comprises, as functional substances:

Poliprotect®: complex of polysaccharides (obtained from *Aloe vera*, *Malva sylvestris* and *Althea officinalis*) and the minerals limestone and nahcolite;

flavonoid fraction (obtained from *Matricaria recutita* and *Glycyrrhiza glabra*).

Composition C comprises: E-Gastryal (hyaluronic acid, hydrolysed keratin, tara gum, xanthan gum, purified water), magnesium alginate, sucralose, potassium sorbate, sodium benzoate, e-polylysine, flavouring, purified water.

ii) Study Design

The model used is a reconstituted human esophageal epithelium (HOE2E/S/5), produced by Episkin®, Lyon (F).

The aforesaid compositions A, B and C (paragraph i) were tested for their film forming properties on a reconstituted human esophageal epithelium (HO2E/S/5) as a biological model under different pH conditions: standard=pH 7.0 and acidic conditions=pH 3.3.

The reconstituted human epithelium models in vitro are close to human tissues in vivo in terms of morphology (multilayer or epithelium) and biochemical and physiological properties and today represent the most promising alternative to animals (ex vivo) for the assessment of topically applied products (Gordon et al., 2015, Zuang V. 2016).

In particular, an assessment was made of:

the kinetics of caffeine penetration (film forming effectiveness) induced by products A, B and C and they were compared with the negative control (NC) and the positive control (V).

Protocol: 0.5 cm$^2$ of reconstituted human esophageal epithelium (HOE2E/S/5) was used. HO2E/S/5 was removed from the nutrient agar solution under a laminar flow cabinet. The inserts were transferred onto a 6-well plate previously filled with a maintenance medium (1 ml/well) at room temperature and incubated overnight at 37° C., 5% CO2, saturated humidity.

Kinetics of Caffeine Penetration (Film Forming Effectiveness):

15 minutes, 1 hour and 2 hours after the application, the fluid of the receptor (saline solution 1 ml) was collected in test tubes (stored at 2-8° C. for the analysis) and tested for the caffeine content with the HPLC technique.

The controls and compositions were evaluated in three biological replicates.

iii) Results

As foreseen, the reference product petroleum jelly (V) almost totally inhibits caffeine penetration. The effectiveness of the compositions A, B and C was quantified as % caffeine considering 100% of the dose quantified in the negative control (NC); the results are summarised in Tables 7 and 8 and in FIGS. 7 and 8.

Under both test conditions (pH 7 and pH 3.3) the maximum reduction in the passage of caffeine was observed with the composition according to the present invention (A, GERDOFF®). In particular, under standard pH conditions composition A (GERDOFF®) showed the maximum effectiveness overall in reducing the passage of caffeine (effective passage of 59.1% after 2 hours) compared to compositions B (Neobianacid, 83.2%) and C (Marial gel, 89.4%), Table 7 and FIG. 7. Furthermore, under acidic pH conditions composition A (GERDOFF®) showed the maximum effectiveness overall in reducing the passage of caffeine (effective passage of 50.3%) compared to compositions B (Neobianacid, 75.3%) and C (Marial gel, 83.5%), Table 8 and FIG. 8.

TABLE 7

| | CAFFEINE % in the basolateral compartment relative to the negative control | | | |
|---|---|---|---|---|
| Samples | 15 min | 1 h | 2 h | Total |
| Negative control (NC) | 17.7 ± 0.2 | 43.3 ± 1.9 | 39.0 ± 0.3 | 100.0 ± 1.9 |
| White petroleum jelly (V) | 5.7 | 7.4 | 1.6 | 14.8 |
| GERDOFF ® milk flavour (A) | 11.7 ± 1.6 | 20.7 ± 0.3 | 26.7 ± 1.0 | 59.1 ± 0.8 |
| NEOBIANACID (B) | 8.7 ± 0.8 | 34.2 ± 3.9 | 40.3 ± 0.3 | 83.2 ± 5.0 |
| MARIAL gel (C) | 16.7 ± 0.6 | 35.4 ± 0.7 | 37.3 ± 1.1 | 89.4 ± 0.8 |

TABLE 8

| | CAFFEINE % in the basolateral compartment relative to the negative control | | | |
|---|---|---|---|---|
| Samples | 15 min | 1 h | 2 h | Total |
| Negative control (CN) | 20.8 ± 2.3 | 47.1 ± 1.0 | 32.1 ± 1.5 | 100.0 ± 1.4 |
| Petroleum jelly (V) | 0.2 ± 0.1 | 1.3 ± 1.0 | 1.3 ± 0.6 | 2.7 ± 1.7 |
| GERDOFF ® milk flavour (A) | 12.3 ± 0.9 | 20.4 ± 0.5 | 17.5 ± 1.0 | 50.3 ± 2.0 |
| NEOBIANACID (B) | 7.7 ± 1.1 | 34.7 ± 0.7 | 32.9 ± 0.8 | 75.3 ± 2.3 |
| MARIAL gel (C) | 19.3 ± 0.8 | 35.6 ± 1.3 | 28.6 ± 0.4 | 83.5 ± 2.6 |

The following day the maintenance medium was changed and HO2E/S/5 was pre-wetted with 15 µL of saline solution. After 15 minutes, 30 mg or 30 µl of NC, V, A, B or C were applied for 15 minutes at room temperature. After 15 minutes of application, 100 µl of a 0.5% caffeine solution (CAFFEINE 1 mg/cm$^2$), as a standard solution at pH=7 or an acidic solution at pH=3.3, were directly and evenly applied topically on the epithelium for 2 hours at room temperature.

III.2) Permeability of the Epithelial Barrier:

The paracellular flow was assessed by Lucifer Yellow assay (LY) in the sample obtained in the in vitro test (II.1) from the reconstituted human esophageal epithelium (HOE2E/S/5) treated with NC, V, A, B or C and subsequently with caffeine at the end of the exposure time (2 h), as described above.

FIG. 9 shows the % LY flow at 2 hours versus the % LY at time 0 in the apical compartment under neutral pH conditions. Under neutral conditions, the negative control (CN) had a permeability to Lucifer Yellow of 11.8% after a treatment of 2 hours. The increase in the % LY flow in the positive control (V) is not significant and the values are in the range considering the internal data. In the samples treated with compositions A (Gerdoff®), B or C, the reduction in the passage of LY indicates that the products tested did not modify membrane permeability (A and C) or, as in the case of B, they exerted a protective effect by reducing the passage of LY. Analogous results were obtained under acidic pH conditions (data not reported).

The analysis of the permeability of the epithelial barrier performed by Lucifer Yellow assay thus showed that all of the products tested (A, B and C) did not cause damage to the cell junctions and preserved the integrity of cell-cell adhesion. The results are comparable under both neutral conditions and acidic conditions.

The invention claimed is:

1. A chewable, suckable and/or melt-in-mouth and/or mouth-saliva dissolving composition, comprising:

I) a mixture comprising:

10 mg of sodium hyaluronate, and 400 mg of chondroitin sulphate sodium, 200 mg of aluminium hydroxide or magnesium trisilicate, 100 mg of calcium carbonate;

20 mg of glyceril-debehenate;

15 mg of silicon dioxide; and 10 mg of ammonium glycyrrhizate;

wherein said composition is not to be broken into pieces and/or swallowed rapidly whole or in pieces with saliva, without leaving time for the saliva to dissolve the composition.

2. The composition according to claim 1, wherein at least said sodium hyaluronate, and said chondroitin sulphate sodium, dissolve in the saliva so as to form a viscous gel that adheres to the mucosa from the oral cavity to the stomach.

3. The composition according to claim 1, wherein said chondroitin sulphate sodium is of animal origin and is extracted from an animal selected from the group consisting of: chickens, bovines, swine, fish and crustaceans.

4. The composition according to claim 1 wherein said chondroitin sulphate is chicken chondroitin sulphate sodium.

* * * * *